US009949713B2

(12) United States Patent
Schonfeld et al.

(10) Patent No.: US 9,949,713 B2
(45) Date of Patent: Apr. 24, 2018

(54) SYSTEM FOR MONITORING CLEANING EFFORTS OF CARE GIVERS USING STETHOSCOPES

(71) Applicants: Alvin J. Schonfeld, Chicago, IL (US); Ryan A. Schonfeld, Hawthorne, CA (US)

(72) Inventors: Alvin J. Schonfeld, Chicago, IL (US); Ryan A. Schonfeld, Hawthorne, CA (US)

(73) Assignee: CLEAN SCOPE, LLC., Chicago, IL (US)

(*) Notice: Subject to any disclaimer, the term of this patent is extended or adjusted under 35 U.S.C. 154(b) by 0 days.

(21) Appl. No.: 14/868,749

(22) Filed: Sep. 29, 2015

(65) Prior Publication Data

US 2016/0089214 A1  Mar. 31, 2016

Related U.S. Application Data

(60) Provisional application No. 62/056,728, filed on Sep. 29, 2014.

(51) Int. Cl.
*A61B 90/70* (2016.01)
*A61B 7/02* (2006.01)
(Continued)

(52) U.S. Cl.
CPC ............... *A61B 7/02* (2013.01); *A61B 7/00* (2013.01); *A61B 90/70* (2016.02); *A61B 90/90* (2016.02);
(Continued)

(58) Field of Classification Search
CPC ..................................................... A61B 90/70
See application file for complete search history.

(56) References Cited

U.S. PATENT DOCUMENTS

| 6,018,835 A | 2/2000 | Schonfeld |
| 8,795,438 B2 | 8/2014 | Rubin et al. |
| 2011/0197921 A1* | 8/2011 | Rubin ................. A61L 2/28 134/18 |

OTHER PUBLICATIONS

International Bureau of WIPO; International Preliminary Report on Patentability in re International PCT Patent Application PCT/US20115/052882; Apr. 13, 2017; 1 page.
(Continued)

*Primary Examiner* — Jason Ko
(74) *Attorney, Agent, or Firm* — Law Office of John W. Harbst

(57) ABSTRACT

A system for monitoring cleaning and sanitization efforts of care givers using stethoscopes including one or more sanitizing and cleaning stations capable of cleaning and sanitizing a head portion of a stethoscope presented thereto. The system includes an identification apparatus operably associated with each of a plurality of stethoscopes. The identification apparatus serves to identify a particular stethoscope and, thus, a particular care provider. An apparatus for detecting each time a particular stethoscope is presented to a sanitizing and cleaning station for effecting a cleaning and sanitization event forms part of the system. An analysis unit is operably connected to each identification apparatus and detecting apparatus and is configured for calculating the cleanliness and sanitization level of each stethoscope as a function of the number of cleaning and sanitization events detected by the detecting apparatus. A method for monitoring cleaning and sanitization efforts of care providers is also disclosed.

13 Claims, 11 Drawing Sheets

(51) Int. Cl.
    *A61L 2/18*      (2006.01)
    *G06Q 10/06*    (2012.01)
    *A61B 7/00*      (2006.01)
    *A61L 2/00*      (2006.01)
    *A61B 90/90*    (2016.01)
    *A61B 90/98*    (2016.01)
(52) U.S. Cl.
    CPC ................ *A61B 90/98* (2016.02); *A61L 2/00* (2013.01); *A61L 2/18* (2013.01); *G06Q 10/06* (2013.01)

(56) References Cited

OTHER PUBLICATIONS

International Searching Authority; Written Opinion of the International Searching Authority in re International PCT Patent Application PCT/US2015/052882; Apr. 13, 2017; 6 pag.

\* cited by examiner

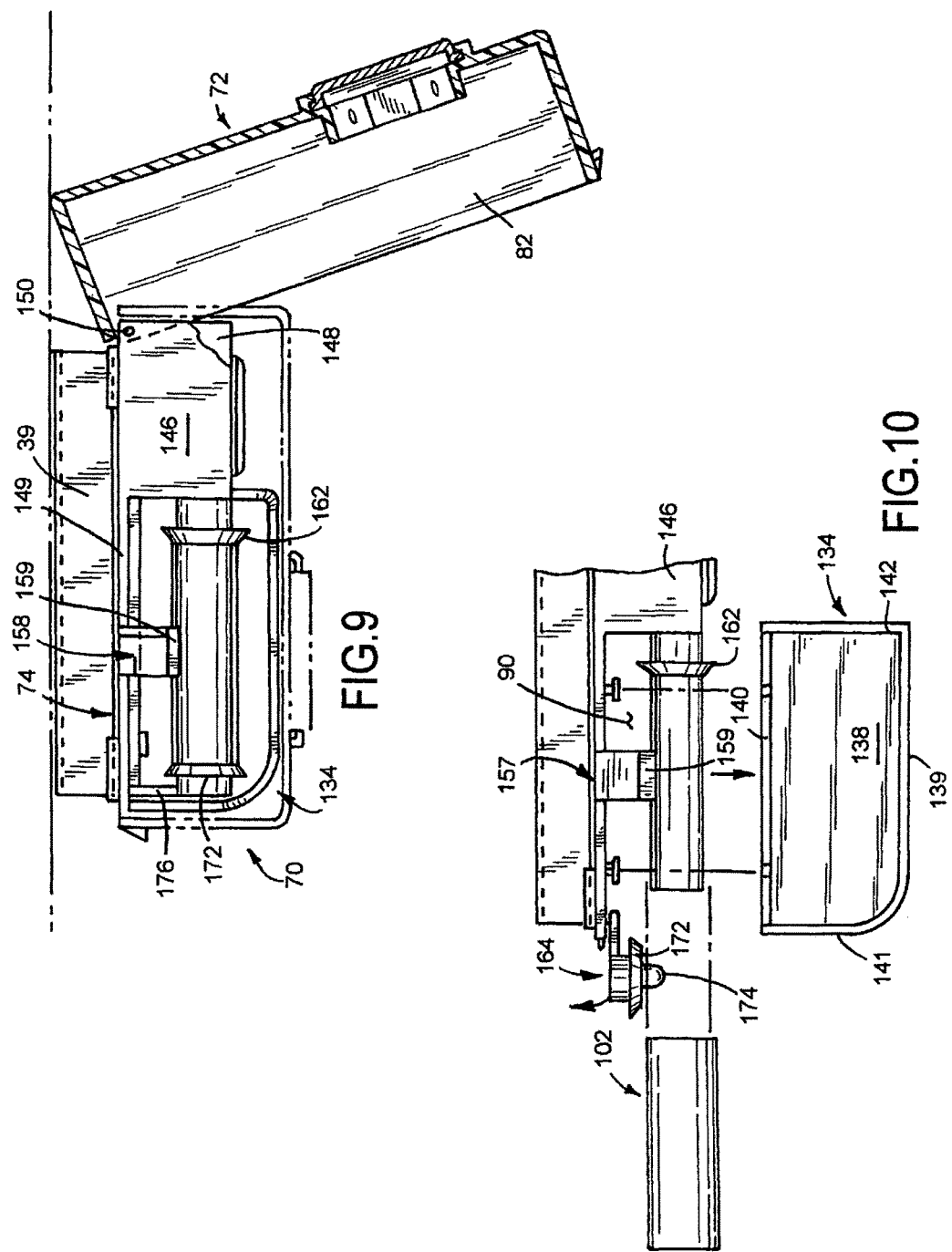

ns, including<br>viruses such as human immunodeficiency virus (HIV)

SYSTEM FOR MONITORING CLEANING EFFORTS OF CARE GIVERS USING STETHOSCOPES

RELATED APPLICATION

This application claims priority under 35 U.S.C. Section 119 to U.S. Provisional Patent Application Ser. No. 62/056,728, filed Sep. 29, 2014, entitled SYSTEM AND RELATED METHOD FOR MONITORING CLEANING AND SANITIZATION EFFORTS OF CARE GIVERS USING STETHOSCOPES, the entirety of which is incorporated by reference herein.

FIELD OF THE INVENTION DISCLOSURE

The present invention disclosure relates to a system and related method for monitoring cleaning and sanitization efforts of care givers using stethoscopes.

BACKGROUND OF THE INVENTION DISCLOSURE

More than one million people get sick each year from infections they contract in hospitals. This has resulted in as many as 100,000 deaths. Fighting these infections costs the healthcare system about $30 billion dollars every year. These statistics are just for hospitals in America. The number of people affected and costs worldwide are considerably greater.

Significant advances have been and are continuing to be made in the field of medical technology. An important and invaluable medical tool to health care providers including doctors, nurses and technicians and which is used in connection with and has lead to such advances is a stethoscope having a head or chest portion. Care givers routinely use stethoscopes to facilitate a patient's medical care by examining the chest, abdomen, and other areas of the patient. Patients in hospitals and related medical facilities often require a greater extent of medical care such as surgery and related invasive procedures which can often leave open wounds. The bodily fluids secreted from such open wounds may be contaminated with infectious agents, including viruses such as human immunodeficiency virus (HIV) thereby resulting in possible contamination of the head portion of the stethoscope.

Multiple types of stethoscopes are commonly used by care givers or health care providers. A care giver can use an inexpensive stethoscope that is typically disposed of after each use such as in intensive care units (ICU's and the like) or ward where VRE (Vancomycia Resistant *Enterococcus*) or MRSA (*Methacillia* Resistent Staph, *Aureus*) and related infections are commonly located. Such disposable stethoscopes, however are usually ill fitting to the care giver, poor quality, and often inadequate for detecting subtle human abnormalities. Electronic stethoscopes are also known in the art. Moreover, most physicians and nurses prefer to use their own individual stethoscope. As used herein and throughout, the term or phrase "stethoscope" is intended to include all such types of instruments used to detect and study sounds produced in a body.

A risk of spreading infections with a stethoscope exists because of its routine use by health care providers throughout the day on multiple patients. Although care givers work with only the best intentions of the patient as their paramount concern, often times and whether by inadvertence or laziness, a care giver will use a stethoscope on one person/patient and, then, reuse the same stethoscope without specific cleaning and sanitation measures being effected between patients. To inhibit the spread of infection, some care givers will wipe the head portion of the stethoscope with an alcohol swab between patients. Such cursory cleaning and sanitization efforts, however, are often inadequate to completely destroy infectious contaminants on the diaphragm of a stethoscope and are often infrequently used between persons/patients. Also, the design of some stethoscopes makes effective wiping of the head or chest portion thereof difficult.

As will be appreciated, medical emergencies only serve to exacerbate these problems. Often times, care givers simply do not have the time necessary and required to adequately clean and sanitize the head or chest portion of their stethoscope between persons/patients. Moreover, and during rounds, doctors are required to frequently pass from one patient's room to another and yet are expected to have enough time to thoroughly and carefully examine each patient. Reusing the stethoscope without sufficient and cleaning and sanitization care being provided thereto often results in the inadvertent but yet positive transference of nosocomial infection or cross contamination between persons/patients.

Thus, there is a need and continuing desire for a system and related method for monitoring cleaning and sanitization efforts of health care givers/providers using stethoscopes.

SUMMARY

In view of the above, and in accordance with one aspect of this invention disclosure, there is provided a system for monitoring cleaning and sanitization efforts of care givers using stethoscopes. According to this aspect, such a system includes one or more sanitizing and cleaning stations capable of cleaning and sanitizing a head portion of a stethoscope presented thereto. The cleaning stations form part of a network used to monitor cleaning and sanitization efforts of health care providers/givers using stethoscopes. The system also includes an identification apparatus operably associated with and assigned to each one of a plurality of stethoscopes. The identification apparatus has a specific code identifying a particular stethoscope and, thus, a particular health care provider. In one form, an apparatus for detecting each time the identification apparatus attached to the particular stethoscope is presented to a sanitizing and cleaning station for effecting a cleaning and sanitization event forms part of the system. An analysis unit is operably connected and responsive to each detecting apparatus and identification apparatus. The analysis unit is configured for calculating the cleanliness and sanitization level of each stethoscope having the identification apparatus operably associated therewith.

As used and throughout, and as will be appreciated, the "cleanliness and sanitization level" of a particular stethoscope following a cleaning event can be evaluated using a number of different factors. One of the factors used in determining the "cleanliness and sanitization level" of a particular stethoscope following a cleaning event can include, but is not limited to, the number of cleaning and sanitizing events each particular stethoscope is subjected to during a given period of time. Another factor used in determining the "cleanliness and sanitization level" of a particular stethoscope can include, but is not limited to, the time period each stethoscope is presented to a cleaning and sanitization station to effect a cleaning event. Another factor used in determining the "cleanliness and sanitization" of a particular stethoscope following a cleaning event can include the cleaning medium used to clean and sanitize the stethoscope. Any number of other additional factors can be used and calculated by the analysis unit to determine and evaluate the "cleanliness and sanitization level" of a particular stethoscope.

In one embodiment, the cleaning and sanitization event at each cleaning station is recorded only after the detection apparatus senses the presence of the cleaning head or chest portion of a particular stethoscope is disposed relative to a sanitizing and cleaning station for a predetermined time period. Preferably, a network repository is provided for storing each time a particular stethoscope is presented to one of the sanitizing and cleaning stations for a cleaning and sanitization event. Moreover, an apparatus is preferably provided for detecting a wearing event for each stethoscope. In this later embodiment, and to account for vacation and other types of absences during which a care taker's personal stethoscope may not be used, the system preferably includes such an apparatus, operably connected to the analysis unit, for partly evaluating the cleaning and sanitization efforts associated with a particular stethoscope based on data indicative of the number of wearing events for each stethoscope.

According to one embodiment, an apparatus can be operably connected to the analysis unit for providing an indication of the cleanliness and sanitization level of any particular stethoscope in the group of stethoscopes. In a preferred embodiment, the sanitizing and cleaning station includes an enclosure defining a port through which the head or chest portion of the stethoscope moves to effect the cleaning and sanitization event. The detecting apparatus is preferably arranged is a position to sense and monitor the ingress and egress of the head or chest portion of the stethoscope through the port in the cleaning station.

According to another aspect of this invention disclosure, the system for monitoring cleaning and sanitization efforts of care givers using stethoscopes includes a plurality of sanitizing and cleaning stations disposed at different locations throughout a facility. Each sanitizing and cleansing station is capable of cleaning and sanitizing a head portion of a stethoscope presented thereto. In this embodiment, an identification apparatus is operative to identify an individual stethoscope in a group of stethoscopes. Moreover, a detection apparatus is associated with each sanitizing and cleaning station. Each detection apparatus is operative to determine the identity of each stethoscope presented to any one of the sanitizing and cleaning stations for a cleaning event. Also, the detection apparatus is operative to detect the time an individual stethoscope is presented to one of the sanitizing and cleaning stations for a cleaning event. An analysis unit is operative to use data from the detection apparatus associated with each sanitizing and cleaning station to determine the cleanliness and sanitization level of each stethoscope having the identification apparatus arranged in operable combination therewith.

Preferably, each cleaning and sanitization event is recorded only after the detection apparatus senses the presence of the cleaning head of a particular stethoscope is disposed relative to one of the sanitizing and cleaning stations for a predetermined time period. According to this aspect of the present invention disclosure, a repository is provided and configured for storing each time a particular stethoscope is presented to one of the sanitizing and cleaning stations for a cleansing and sanitization event. In one embodiment, an apparatus for detecting a wearing event for each stethoscope is provided as part of the system; with the cleaning and sanitization effort, associated with a particular stethoscope, being partially evaluated as a function of the number of wearing events detected by the apparatus for detecting wearing events.

Optionally, the system further includes an apparatus operably connected to the analysis unit for displaying an indication of the cleanliness and sanitization level of a particular stethoscope. In one form, each sanitizing and cleaning station includes an enclosure defining a port through which the head portion of the stethoscope moves to effect the cleaning and sanitization event. Preferably, the identification apparatus is arranged is a position to sense the ingress and egress of the head portion of the stethoscope through the port in such enclosure.

According to another aspect of this invention disclosure, there is provided a method for monitoring cleaning and sanitization efforts of care givers using stethoscopes. Such method involves the steps of: establishing a relationship between a care giver and a particular stethoscope, and providing a sanitizing and cleaning station capable of cleaning and sanitizing a portion of a stethoscope presented thereto for cleaning and sanitization. The method also involves detecting when each individual stethoscope is presented to one of the sanitizing and cleaning stations to effect a cleaning and sanitizing event. According to this aspect, the method also involves evaluating the cleanliness and sanitization level of each stethoscope.

Preferably, another step in the method of monitoring cleaning and sanitization efforts of persons using stethoscopes involves recording when an individual stethoscope is presented to the sanitizing and cleaning station for a cleaning and sanitizing event only after each individual stethoscope is presented to the sanitizing and cleaning station for a predetermined period of time. Another step in the methodology preferably includes: storing in a repository each time an individual stethoscope is presented to the sanitizing and cleaning station for a cleaning and sanitizing event.

Such a method can preferably also include the step of: detecting a wearing event for each stethoscope; with each cleaning and sanitation effort being partially evaluated according to the number of wearing events for a particular stethoscope. In one form, each sanitizing and cleaning station includes an enclosure defining a port through which the head portion of the stethoscope moves to effect the cleaning and sanitization event. The step of determining and recording when each individual stethoscope is presented to the sanitizing and cleaning station for a cleaning and sanitizing event is accomplished by a detection mechanism arranged is a position to sense the ingress and egress of a portion of each stethoscope through the port associated with said sanitizing and cleaning station. Preferably, such method for monitoring cleaning and sanitization efforts of care givers using stethoscopes also includes the further step of: comparing the number of cleaning and sanitization events for a particular stethoscope against a predetermined value to determine the cleanliness and sanitization level of the particular stethoscope.

According to still another aspect of this invention disclosure, there is provided a stethoscope including a pair of ear pieces which are adapted to fit into ears of a health care provider so as to transmit sounds directly into the healthcare provider's ears. The stethoscope further includes a pair of hollow ear tubes, with one ear tube extending from each ear piece to transmit sounds detected by a chest piece of the stethoscope. A flexible acoustic tube leads from and operably joins the hollow ear tubes to the chest piece. As is typical, the chest piece captures sounds from a target area on a patient and delivers the sounds to the acoustic tube for ultimate delivery to the ear pieces. According to this aspect of the invention disclosure, the stethoscope further includes an apparatus operably associated with the stethoscope for providing an electronically and automatically readable signature indicative of the identity of the stethoscope.

BRIEF DESCRIPTION OF THE DRAWINGS

FIG. 9 is a top plan view with a cover of the sanitizing and cleaning station shown in section and moved to a position to show an interior of the sanitizing and cleaning station;

FIG. 10 is a fragmentary view similar to FIG. 9 but showing various components of the sanitizing and cleaning station in disassembled relation relative to each other;

DETAILED DESCRIPTION

Figure 1:
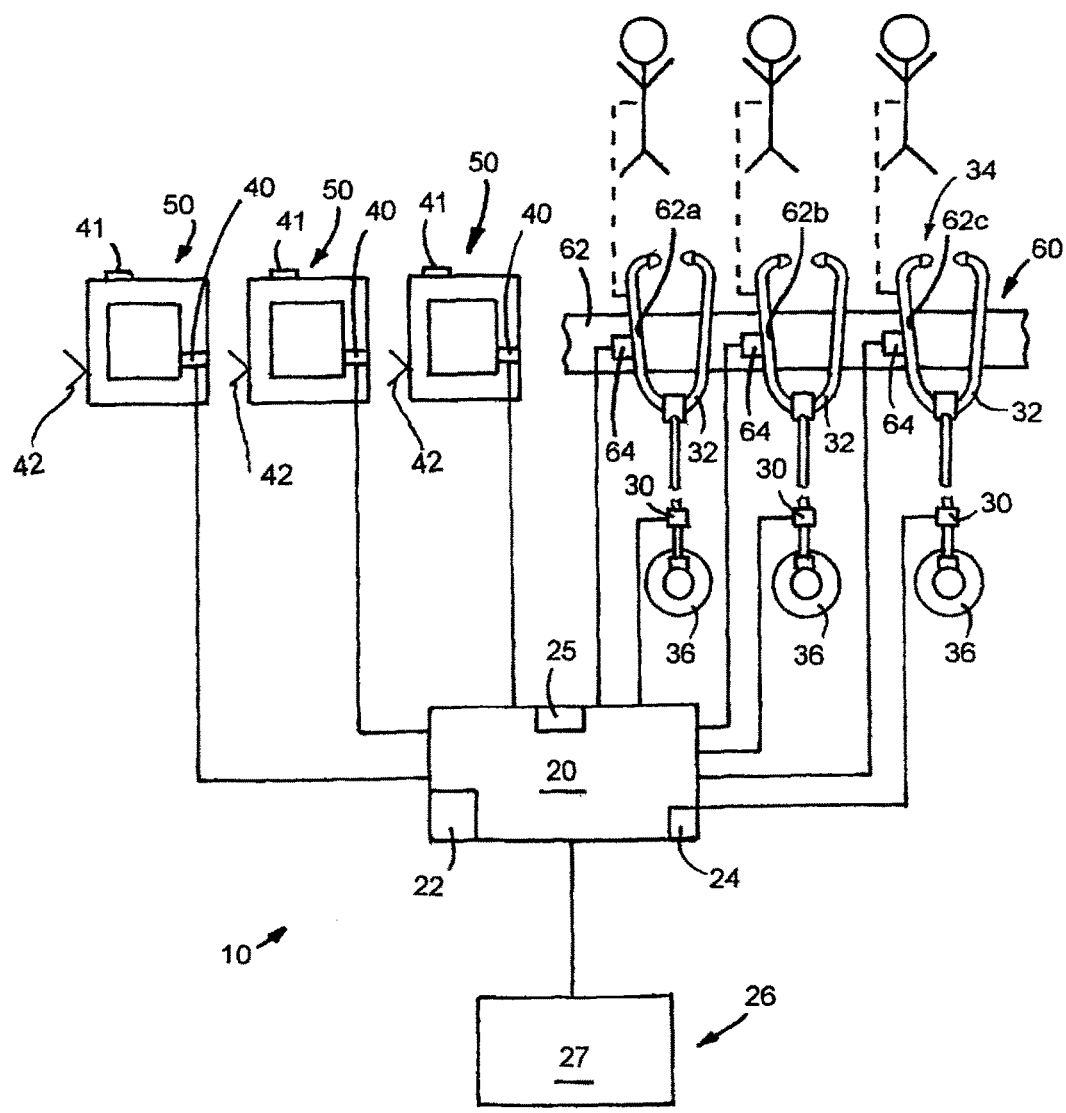
FIG. 1 is a schematic illustration of one embodiment of a system for monitoring cleaning and sanitization efforts of care givers using conventional stethoscopes.

The following detailed description is directed to a system and method for monitoring cleaning and sanitization efforts of care givers using stethoscopes. As described briefly above, nosocomial and related infections are a significant concern to hospitals, emergency care facilities, doctor's offices and other patient care facilities around the world. In many cases, nosocomial and related infections may be controlled through the establishment of and adherence to proper sanitization procedures, including cleaning and sanitization of stethoscopes.

Utilizing the concepts and technology disclosed herein, a system and related method for monitoring cleaning and sanitization efforts of care givers using stethoscopes in patient care facilities is provided whereby enhancing opportunities for those care givers using stethoscopes to become more aware of the cleanliness and sanitization levels of such medical devices and equipment. As will be explained in greater detail below, and in some embodiments of this invention disclosure, reports can be generated to identify the care giver and/or health care provider who have not taken those positive steps to ensure the cleanliness and sanitization levels of their stethoscope.

By utilizing various aspects of the invention disclosure provided below, health care personnel can be reminded when they need to clean and sanitize their stethoscope. By utilizing various aspects of this invention disclosure provided below, reports can be generated alerting others to the level of cleanliness and sanitization care being effected by such individuals. Patients are thereby provided with significantly enhanced protection against infections being inadvertently being transferred between patients through use of contaminated stethoscopes. It should furthermore be appreciated various embodiments of this invention disclosure can be used in any of several different environments, i.e., hospitals, doctors's offices and other patient care environments which would all undoubtedly receive a tremendous benefit from preventing the spread of germs via simple cleansing and sanitization of the stethoscopes used therein.

While this invention disclosure is susceptible of embodiment in multiple forms, there is shown in the drawings and will hereinafter be described preferred embodiments, with the understanding the present disclosure is to be considered as setting forth exemplifications of the invention disclosure which are not intended to limit the disclosure to the specific embodiments illustrated and described.

Referring now to the drawings, wherein like reference numerals indicate like parts throughout the several views, there is schematically illustrated in FIG. 1 a system, generally indicated by reference numeral 10, for monitoring cleaning and sanitization efforts of care givers using conventional stethoscopes. Optionally, system 10 both operably tests the compliance of care givers using stethoscopes with given standards and tests the quality of the cleaning and sanitization of the stethoscopes used by such healthcare providers. In one form, system 10 includes an analysis unit 20 which preferably includes a suitable programmable computer 22 including a processor 24. Optionally, the analysis unit 20 further includes a repository 25 for storing each time a particular stethoscope 32 in a group of stethoscopes 34 is presented for a cleaning and sanitization event. Moreover, the analysis unit 20 can be structured and programmed to perform an analysis of the cleaning and sanitization efforts of any one or a plurality of healthcare providers based on a number of factors including, but not limited to: time logs of the healthcare providers; logged cleaning and sanitization events; statistical analysis of recorded cleaning and sanitization events; a comparison, optionally statistical, of recorded stethoscope cleaning and sanitization events of others, and, any one or more related dynamic factors which may be considered important to the cleanliness and sanitization level of any one or more stethoscopes.

The analysis unit 20 is operably connected to and receives data from one or a plurality of personal identification devices 30. Each personal identification apparatus 30 is operably associated with a particular stethoscope 32 in the group of stethoscopes 34. In turn, each stethoscope 32 is related to or associated with a certain person/user, such as a care giver, for example a nurse, a physician, a paramedic, a researcher, a member of a emergency medical service, and etc. whereby establishing a relationship between a care giver/health care provider and a particular stethoscope 32 in the group of stethoscopes 34.

System 10 further includes an apparatus 26 operably connected and responsive to the analysis unit 20 for providing an indication of the cleanliness and sanitization level to the person/care giver associated with each respective stethoscope based on the number of factors some of which were listed above. Optionally, such apparatus 26 includes a suitable printer device 27 for printing or otherwise providing an indication of the cleanliness and sanitization level of any particular stethoscope in the group of stethoscopes 34.

Each identification apparatus or device 30 is operative to identify both a person/care giver and a particular stethoscope 32 in the group 34 of conventional stethoscopes. As schematically illustrated in FIG. 1, and as is conventional, each stethoscope 32 includes a head portion 36. Optionally, each identification apparatus or device 30 can be in the form of a tag or the like having a readable code imprinted or otherwise provided thereon and wherein such code identifies a particular stethoscope 32 as well as the care giver/healthcare provider to whom the particular stethoscope is assigned. In another form, the identification apparatus 30 operably associated with each stethoscope 32 includes an apparatus for providing an electronically and automatically readable signature indicative of the identity of the stethoscope and, thus, the person to whom the stethoscope is assigned.

Optionally, such identification apparatus 30 can be in the form of an RFID (Radio Frequency Identification) tag, a tag having a magnetic strip, an Optical Character Recognition (OCR) smart card, or other suitable device for automatically providing a personal identification characteristic of the stethoscope and the person to whom the stethoscope is assigned and which allows data to be automatically collected and delivered to the analysis unit 20 for further evaluation and consideration. A suitable reader for automatically sensing and recording the presence of the identifying apparatus 30 may be arranged at the entrance to a patient's room or other suitable location within the facility. While only three stethoscopes 32 in the group of stethoscopes 34 are illustrated for exemplary purposes, it will be appreciated, the present invention disclosure is equally applicable and adaptable to a system and/or network for monitoring cleaning and sanitization efforts of tens if not hundreds of care givers; with each care giver being personally assigned to a particular stethoscope.

In one form, the analysis unit 20 is operably connected to a detection apparatus or mechanism 40 arranged in operable combination with each of one or more sanitizing and cleaning units or stations 50 arranged or disposed at different locations throughout a facility. The detection mechanism 40 on each sanitizing and cleaning station 50 operates in combination with the identification apparatus 30 and is operative to determine the identity of each particular stethoscope 32 presented to any one or more of the plurality of stations 50 for cleaning and sanitization. More specifically, the detecting apparatus 40 is operative to automatically detect each time the identification apparatus 30, attached and assigned to a particular stethoscope, is presented to a cleaning and sanitization station 50 to effect a cleaning and sanitization event. Preferably, the detection mechanism 40 operates in operable combination with the analysis unit 20 to detect the duration of the cleaning event during which an individual or personal stethoscope 32 is presented for cleaning and sanitization to one of the cleaning and sanitization stations 50.

It will be appreciated, the number of sanitizing and cleaning stations 50 arranged in combination with and forming a part of system 10 will be dependent upon the size of the facility wherein system 10 is utilized. For example, a doctor's office may require only one or limited number of cleaning and sanitization stations 50. On the other hand, a hospital or other relatively large facility can require many more cleaning and sanitization stations 50 to be formed as part of system 10. Suffice it to say, the system 10 of this invention disclosure is equally applicable and adaptable to a monitoring system having a single and/or hundreds of cleaning and sanitizing stations arranged as part thereof.

The analysis unit 20, the identification apparatus 30 associated with each stethoscope 32 in the group of stethoscopes 34, and the detection devices 40 in the system 10 all preferably communicate through a conventional wired network, for example a local area network (LAN) and wide area network (WAN), or a wireless network, for example a wireless LAN (WLAN) and/or a wireless personal area network (WPAN).

As mentioned, a detection apparatus 40 is arranged in proximate relation to each cleaning and sanitization unit or station 50 arranged or disposed at different locations throughout the facility, i.e., proximate each patient's room or each examination room in a facility. In one form, the detection apparatus 40 and cleaning station or unit 50 can be arranged in close proximity to the patient/person receiving care such that the person receiving such care can see and appreciate the health care worker is cognizant of the risks involved with the possibility of an inadvertent transference of infections and is taking positive steps to clean and sanitize their stethoscope. The detection apparatus 40 at each cleaning and sanitization station 50, in whatever form, is operative to determine the identity of each stethoscope 32 presented to a station 50 for cleaning and sanitization. As discussed further below, the detection apparatus 40 at each cleaning and sanitization station 50 is furthermore preferably operative to detect the time an individual or personal stethoscope is presented to one of the cleaning and sanitization units 50 for a cleaning event to be performed thereon, and, optimally, the duration of such cleaning event.

Each sanitizing and cleaning station 50 of system 10 operably serves to clean, sanitize and preferably disinfect the head portion 36 of the stethoscope 32 presented thereto. It should be appreciated from an understanding of the present disclosure, however, the cleaning and sanitization station 50 can come in many different designs and forms without detracting or departing from the broad spirit and novel scope of this invention disclosure.

In a preferred embodiment, and to reduce energy consumption, each cleaning and sanitization station 50 operates in either an "operational" mode or a "stand-by" mode of operation. Typically, each cleaning and sanitization station 50 is in a "stand-by" mode of operation during which operation energy consumption is minimized. When a health care provider having a stethoscope with a identification apparatus 30 arranged in operable combination therewith comes within a specified radius of a cleaning and sanitization station 50, however, the detection apparatus or its equivalent is automatically switched to an "operational"

mode of operation. In a preferred form, it will be appreciated, when the health care provider having a stethoscope with a identification apparatus 30 arranged in operable combination therewith leaves such predetermined radius, the cleaning and sanitization station 50 automatically returns to the "stand-by" mode of operation.

Figure 2:
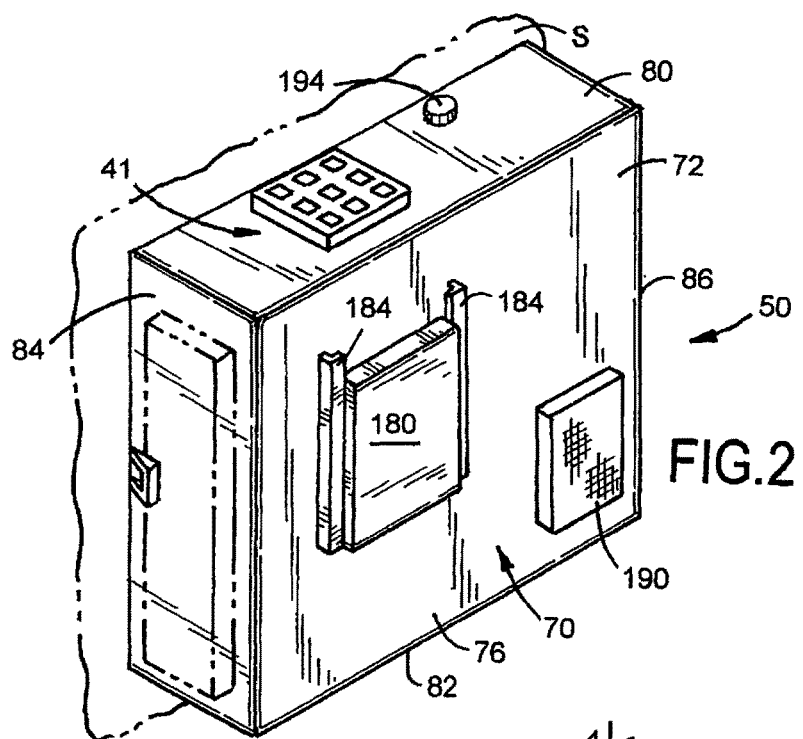
FIG. 2 is a perspective view showing one example of a sanitizing and cleaning station forming part of the system for monitoring cleaning and sanitization efforts of care givers using conventional stethoscopes.
Figure 3:
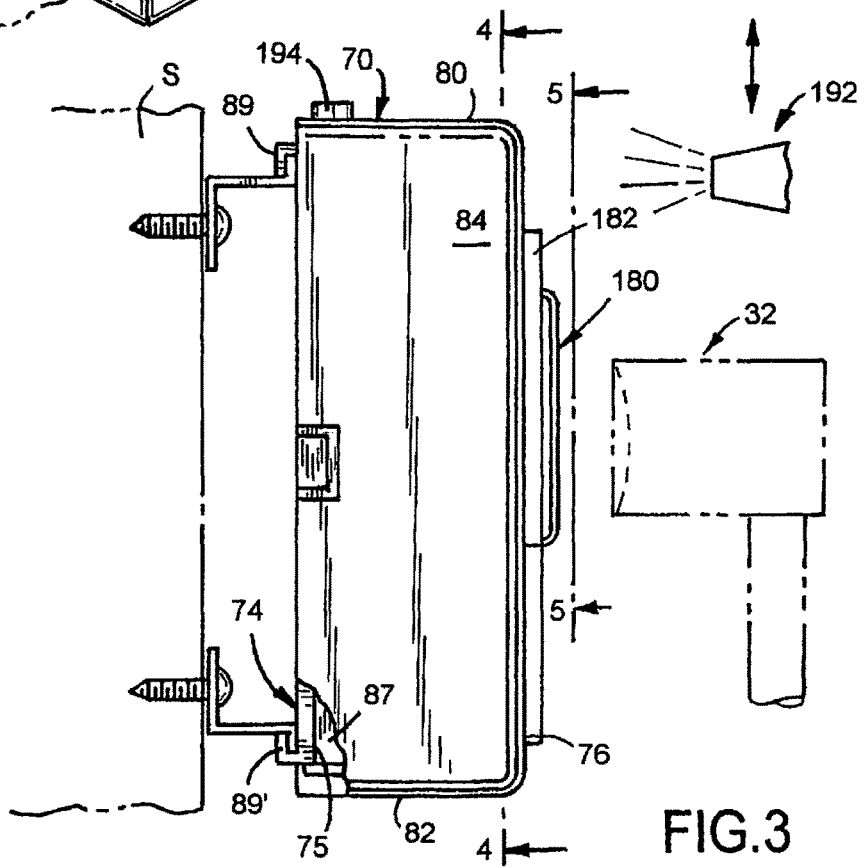
FIG. 3 is an enlarged side elevational view of the sanitizing and cleaning station illustrated in FIG. 1 attached to a suitable support surface and showing a stethoscope about to be inserted to effect a cleaning and sanitization event.

In one form shown in FIG. 2, the cleaning and sanitization station 50 includes a housing 70 of multi-walled construction. In one form, housing 70 includes a cover 72 mounted in releasable and sealable association with a base 74 (FIG. 3). Preferably, cover 72 and base 74 are formed from plastic or other material that is non-permeable to liquids. Cover 72 is preferably of uni-body constructions and, in the illustrated example, includes a front wall portion 76 with multiple wall portions extending rearwardly therefrom. In the illustrated embodiment, cover 72 includes top and bottom generally parallel wall portions 80 and 82, respectively, rigidly joined to opposed and generally parallel side wall portions 84 and 86, with all the wall portions 80, 82, 84 and 86 being joined to each other and extending rearwardly from the front wall portion 76.

As shown in FIG. 3, the base 74 of housing 70 is configured with suitable brackets 89 and 89' extending rearwardly therefrom for facilitating releasable attachment of housing 70 to a stationary support surface S. As will be appreciated, the brackets 89 and 89' for releasably attaching housing 70 to the support surface S can take a form other than that shown for exemplary purposes without detracting or departing from the spirit and scope of this invention disclosure. For example, apertured hangers or mating lengths of Velcro® or the like can be attached to or formed into the housing 70.

Figure 7:
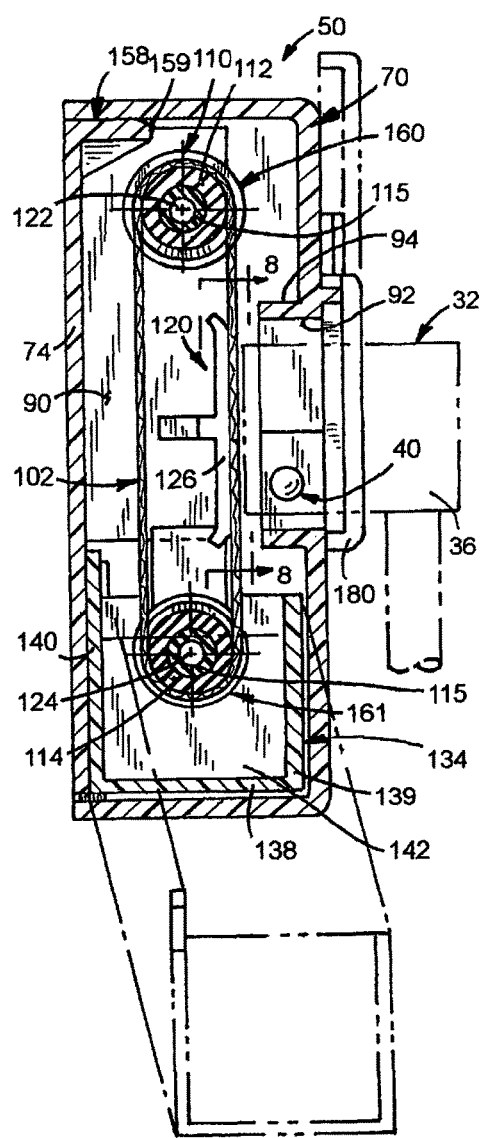
FIG. 7 is a cross-sectional view taken along line 7-7 of FIG. 4 and illustrating a head portion of the stethoscope inserted for a cleaning event in the sanitizing and cleaning station.

In the example shown, housing 70 defines an interior cleaning chamber 90 (FIG. 4) defined between interior surfaces 87 of the cover 72 and an interior surface 75 of the base 74. As shown in FIGS. 5 and 7, an inlet or opening 92 is preferably defined in the front wall portion 76 of housing 70. In one form, the inlet opening 92 extends between the exterior of housing 70 and the cleaning chamber 90 (FIG. 7) for allowing insertion of the head portion 36 of the stethoscope 32 into the chamber 90 for a cleaning and sanitation event to be performed thereon.

Figure 6:
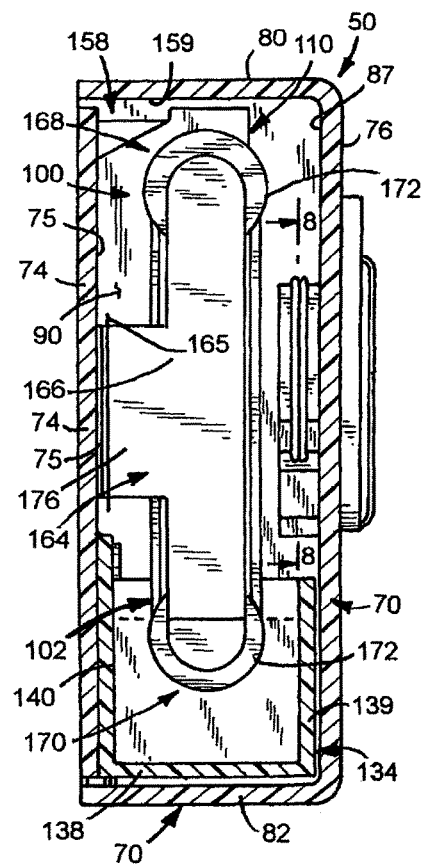
FIG. 6 is an enlarged cross-sectional view taken along line 6-6 of FIG. 4.
Figure 8:
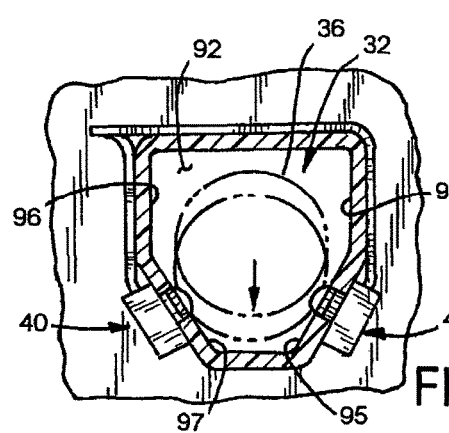
FIG. 8 is an enlarged cross-sectional view taken along line 8-8 of FIG. 7

As shown by way of example in FIG. 8, opening 92 is partially defined by a pair of depending and opposed side walls 94 and 96. The side walls 94, 96 are spaced apart by a distance allowing a head portion 36 of a conventional stethoscope 32 to pass therebetween and into the cleaning chamber 90 (FIG. 6). Preferably, the side walls 94 and 96 of opening 92 are configured to positively position and support the head portion 36 of a conventional stethoscope 32 therebetween and relative to the cleaning chamber 90 without requiring any further support or assistance from a healthcare provider. That is, after the head portion 36 of a conventional stethoscope 32 is inserted into the cleaning chamber 90, gravity, along with the hanging weight of the remainder of the stethoscope, causes the stethoscope head portion 36 to move toward a lower end of the opening 92. As the stethoscope head portion 36 moves downward under gravity toward a lower portion of the opening 92, the walls 94, 96 of opening 92 are specifically configured to isolate and support the head portion 36 of the stethoscope within the chamber 90.

In the embodiment shown by way of example in FIG. 8, the side walls 94 and 96 partially defining opening 92 preferably have a V-shaped configuration extending along at least a portion of their lengths for positively guiding and positioning the head portion 36 of the stethoscope 32 relative to the cleaning chamber 90 (FIG. 6). The side walls 94 and 96, defining opposed sides of opening 92, preferably define camming surfaces 95 and 97 extending along at least a lengthwise portion of the respective side wall 94 and 96 for positively guiding and positioning the head portion 36 of the stethoscope relative to the cleaning chamber 90. Moreover, the side walls 94 and 96 of opening 92 preferably extend rearwardly from the front wall portion 76 of housing 70 and into the cleaning chamber 90 for promoting support of the stethoscope head portion 36 inserted into the chamber 90 for effecting a cleaning and sanitization event without requiring independent support assistance from a health care provider or others.

In the illustrated embodiment of station 50, a cleaning and sanitization mechanism 100 is arranged in chamber 90 of housing 70 for cleaning and sanitizing the head portion 36 of the stethoscope 32 inserted through opening 92. It should be appreciated from an understanding of the present disclosure, the cleaning and sanitization mechanism 100 can come in many different designs and forms without detracting or departing from the broad spirit and novel scope of this invention disclosure. In the embodiment illustrated by way of example in FIG. 6, the cleaning and sanitizing mechanism 100 includes a cleaning member 102 of resilient material such as cloth which tends to absorb and hold, liquid and, yet, will not scratch or abrade the face of the head portion 36 of the stethoscope inserted into chamber 90 for a cleaning and sanitization event. In the illustrated embodiment, the resilient cleaning member 102 is positioned in the cleaning chamber 90 for engagement with face of the head portion 36 of the stethoscope after the head portion 36 of the stethoscope is inserted through the port or inlet opening 92 of housing 70.

Optionally, the resilient cleaning member 102 is configured as a belt and forms part of a rotating drive assembly 110. Drive assembly 110 further includes a pair of roller shafts 112 and 114 arranged for rotation within chamber 90 of housing 70 and about axes 122 and 124, respectively. The axes 122 and 124 extend in general parallel relation relative to each other. As shown, the cleaning belt 102 is entrained in driving relation about the shafts 112 and 114 and rotates therewith. In one form, each shaft 112, 114 has an internal throughbore or hollow core 115 (FIG. 7) opening to opposite ends of the respective shaft.

The shafts 112, 114 are preferably positioned within the chamber 90 whereby a lengthwise portion of the cleaning member 102 is positioned relative to the opening 92 such that when the head/chest portion 36 of a stethoscope is inserted through port 92 and into the cleaning chamber to effect a cleaning and sanitizing event, the cleaning member 102 engages with the head portion 36 of the stethoscope to throughly clean and sanitize the entire head/chest portion 36 of the stethoscope from nosocomial infection and related contaminants. The cleaning member 102 is preferably impregnated with a suitable solution to clean, sanitize and otherwise disinfect the head portion 36 of the stethoscope inserted into engagement therewith. The cleaning solution can be of any suitable anti-bacterial solution which operably sterilizes and effectively disinfects a surface contacted thereby and preferably has a relatively low rate of vaporization. Cleaning solutions such as chlorhexadine or alcohol are but two types of cleaning and sanitizing disinfectants that readily lends themselves to this situation.

Optionally, a support 120 is provided for facilitating cleaning and sanitization of the head portion 36 of the stethoscope 30 once the stethoscope head portion 36 is inserted into the cleaning chamber 90 of housing 70 for a cleaning event to be performed thereon. More specifically, and in the embodiment shown in FIGS. 4 and 7, the base 74 of housing 70 is preferably configured with a plate-like member 126 arranged to one side of the belt 102 opposite from the inlet port or opening 92. The purpose of the member 126 is to support a lengthwise portion of the belt 102, opposite from the inlet opening 92, from deflecting beyond a predetermined limit in response to the stethoscope head portion 36 being placed thereagainst during a cleaning and sanitization event.

Returning to FIG. 4, in the illustrated form, drive assembly 110 further includes a motor 130 for rotatably driving at least one of the shafts 112, 114 and thereby the belt 102 entrained thereabout. The motor 130 is operably connected to a suitable power source 132 which, in the illustrated embodiment, includes batteries 134 but can likewise be any common electrical power source.

Optionally, the housing 70 furthermore preferably includes a removable sump 135 for holding a supply of suitable cleaning solution therein. In the illustrated embodiment, and during operation of drive assembly 110, a lengthwise portion of the belt 102 continually passes through the sump 135 to effect a cleaning action for and to maintain the cleaning member 102 with moisture to thoroughly clean and sanitize the stethoscope head or chest portion 36 during a cleaning and sanitization event. The ability to quickly and readily remove the sump 135 from housing 70 facilitates frequent changing and/or replacement of the cleaning solution within the sump 135. As such, the cleaning solution in the sump 135 can preferably and particularly be suited to the particular infection which may be associated with a particular person/patient being treated and/or examined.

Figure 4:
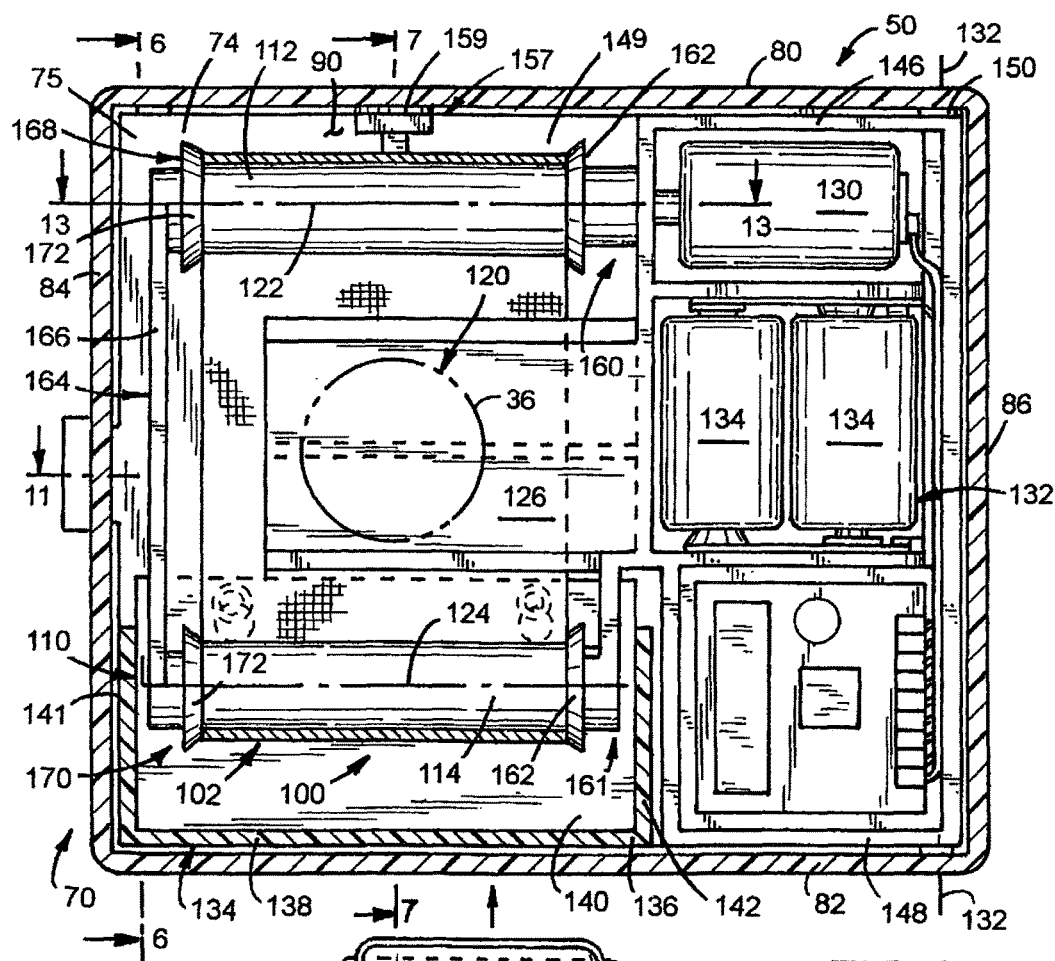
FIG. 4 is an enlarged cross-sectional view taken along line 4-4 of FIG. 3.
Figure 5:
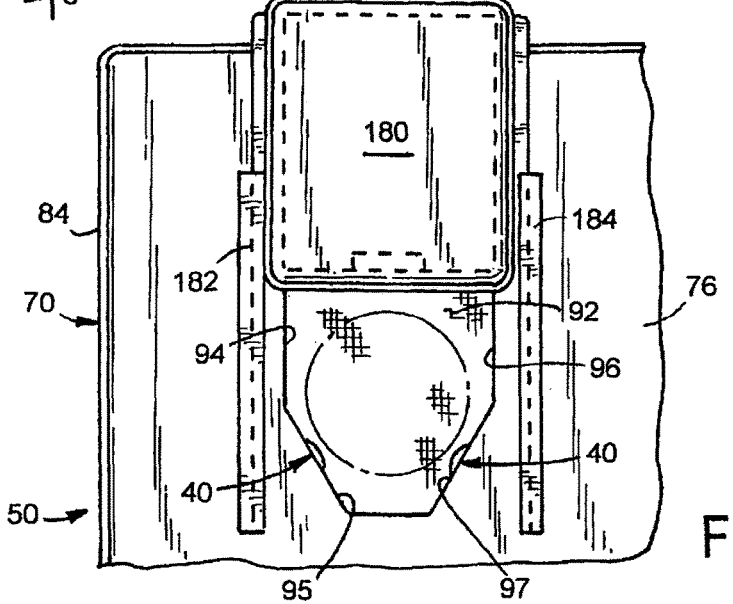
FIG. 5 is an enlarged fragmentary front elevational view taken along line 5-5 of FIG. 3.

In the embodiment shown is FIGS. 4, 6 and 7, sump 135 preferably includes a liquid tight housing 136 for holding a supply of cleaning solution therein. In the form shown by way of example, housing 136 has a bottom wall portion 138 joined to upstanding and laterally spaced front and back wall portions 139 and 140, respectively, and longitudinally spaced end wall portions 141, 142. The wall portions of housing 136 are configured to offer a depth to the housing 136 such that sump 135 can hold a significant amount of cleaning solution therein. In one form, the back wall portion 140 is preferably configured for releasable attachment to the interior surface 75 of base 74. Suffice it to say, the sump 135 is positioned within the cleaning chamber 90 of housing 70 such that at least a portion of the belt 102 entrained about the shafts 112, 114 passes through the cleaning solution in the sump 135 during each cleaning and sanitization event for the stethoscope head portion 36 whereby effecting a continuous disinfecting of the belt 102.

In another form of this invention disclosure, a container for holding a significant amount of cleaning solution therein can be arranged in proximate but separate relation from each housing 70 of the cleaning unit or station 50. Suitable plumbing can be used to connect such a container to the cleaning station unit housing 70 for delivery to the cleaning and sanitization mechanism 100. Moreover, housing 70 can be provided with a suitable drain which leads to a collection system arranged separate from the cleaning station unit housing 70 and wherein waste or used cleaning fluid is collected. As will be appreciated, this alternative version of supplying a cleaning solution to the cleaning station or unit 50 readily lends itself to using different types of cleaning solutions for guarding against inadvertent transference of different types of infections between different patients/persons whereby significantly enhancing the versatility of this invention disclosure in the treatment of different types of infectious and communicable diseases.

As mentioned above, the detection mechanism 40 (FIG. 1) is arranged for sensing and identifying, as through the identification apparatus or sensor 30 (FIG. 1), the particular stethoscope 32 in the group of stethoscopes 34 being presented to the cleaning and sanitization station or unit 50 to effect a cleaning event. In the embodiment illustrated by way of example in FIG. 8, the detection mechanism 40 preferably includes at least one sensor or reader 41 mounted proximate to each cleaning station 50, and in combination with identification apparatus 30 and the analysis unit 20, serves to: 1) monitor which particular stethoscope 32 in the group of stethoscopes 34 is presented to the cleaning and sanitization station or unit 50 to effect a cleaning event; 2) monitor when the particular stethoscope 32 in the group of stethoscopes 34 is presented to the cleaning and sanitization station or unit 50 to effect a cleaning event; and 3) calculate how long the particular stethoscope 32 in the group of stethoscopes 34 is presented to the cleaning and sanitization station or unit 50 to effect a cleaning event.

The detection mechanism 40 can furthermore be used to detect when a care giver/health care provider with a stethoscope having an identification apparatus 30 arranged in operable combination therewith comes within a specified radius of a cleaning and sanitization station 50 so as to automatically switch the mode of operation of the cleaning and sanitization station 50 from "stand-by" mode to an "operational" mode. Moreover, in a preferred embodiment, and unless a cleaning and sanitization event is begun with a predetermined time period of the health car provider with a stethoscope having an identification apparatus 30 arranged in operable combination therewith coming within a specified radius of a cleaning and sanitization station 50, an audible and/or visual alarm will be generated by a suitable apparatus 42 so as to alert/remind the health care provider of the need to clean and sanitize the head portion of their stethoscope. Preferably, such apparatus 42 is arranged on the cleaning and sanitization station 50. Moreover, the detection mechanism 40 can preferably detect when the health care provider with a stethoscope having an identification apparatus 30 arranged in operable combination therewith exits the area of the cleaning and sanitization station 50 whereby returning the cleaning and sanitization station 50 to a "stand-by" mode of operation.

As will be appreciated by those skilled in the art, the sensor 41 of mechanism 40 can take any suitable form for effecting the desired ends. In one form, and during operation, the detection mechanism sensor 41 reads or otherwise detects the personal code operably associated with the identification sensor 30 on each particular stethoscope 32 and signals the analysis unit 20 to indicate which particular stethoscope 32 in the group of stethoscopes 34 is being presented to the cleaning and sanitization station 50 to effect a cleaning event based on the personal code operably associated with the identification sensor 30 on the stethoscope 32. Moreover, and in combination with analysis unit 20, the sensor 41 monitors and detects each time and date the head portion 36 of a particular stethoscope 32 passes the sensor 41 and signals to the analysis unit 20 indicative of each time of that personal stethoscope 32 passes the sensor 41 to effect a cleaning event.

As a function of the signals delivered from the detection mechanism 40, the analysis unit 50 can: 1) determine which particular stethoscope has been presented to the cleaning and sanitization station 50 for a cleaning event; 2) readily determine whether the head/chest portion 36 of a particular stethoscope 36 has been presented to the sanitizing and cleaning unit 50 for a sufficient time to qualify that particular stethoscope as being subjected to a cleaning event; 3) record the time of such cleaning event for a particular stethoscope; and 4) record the date of each cleaning event for a particular stethoscope. Alternatively, the detection mechanism 40 can include more than one sensor or reader 41 operating in unison relative to each other and preferably arranged in proximate relationship relative to the opening or port 92 in housing 70 to accomplish the desired ends and results listed above without detracting or departing from the spirit and broad scope of this invention disclosure.

As mentioned, the detecting mechanism or apparatus 40 for effecting those ends described above, can take different forms from that described above without detracting or departing from the spirit and scope of this invention disclosure. For example, and rather than automatically detecting when a health care provider with a stethoscope having an identification apparatus 30 arranged in operable combination therewith comes within a specified radius of a cleaning and sanitization station 50, each cleaning and sanitization unit 50 can be provided with an apparatus 41' for manually inputting information to the analysis unit 20 so as to identify the particular stethoscope 32 in the group of stethoscopes 34 being presented to the cleaning and sanitization unit 50 for effecting a cleaning event. In one form, such apparatus 41' can include a manually operated key pad or the like which allows the care giver to input a particular code identifying the particular stethoscope 32 to be subjected to a cleaning and sanitization event. Such code would be delivered to the analysis unit 20 for further processing.

In operation, such apparatus 41' would function in operable combination with the detection mechanism or apparatus 40 when the particular stethoscope 32 is presented to the cleaning and sanitization unit 50 to: 1) identify which particular stethoscope 32 in the group of stethoscopes 34 is being presented to the cleaning and sanitization station 50 to effect a cleaning event based on the inputted personal code; 2) readily determine whether the head portion 36 of a particular stethoscope 32 has been presented to the sanitizing and cleaning unit 50 for a sufficient time to qualify that particular stethoscope as being subjected to a cleaning event; 3) record the time of such cleaning event for a particular stethoscope; and 4) record the date of each cleaning event for a particular stethoscope. Also, operation of apparatus 41' can be used to manually switch the cleaning and sanitization unit 50 from the "stand-by" mode of operation to an "operational" mode of operation.

Each sanitizing and cleaning station 50 of system 10 is preferably operated at variable speeds. That is, the detection mechanism 40, in whatever form, furthermore serves to control operation of the respective sanitizing and cleaning station 50 as a function of when mechanism 40 detects or is otherwise operated to indicate the presence of a head portion 36 of a stethoscope being presented to unit 50 for a cleaning event. In one form, sensor 41 forming part of the detection mechanism 40 in whatever form is provided along the length of at least one camming surface 95, 97. As the head portion 36 of the stethoscope 32 is positioned by the caroming surfaces 95, 97 relative to the cleaning chamber 90 and the cleaning mechanism 100, the detection mechanism 40 detects or is otherwise operated to indicate the presence of the head portion 36 of the stethoscope 32 in relation to the cleaning and sanitization unit 50 and signals the motor 130 to operate the cleaning mechanism 100.

To allow service access to the cleaning chamber 90 and, thus, to the cleaning mechanism 100, cover 72 is movably attached to the base 74 of housing 70. As shown in FIGS. 4 and 9, base 74 is provided with generally parallel upper and lower flanges 146 and 148, respectively, projecting forwardly from a back plate 149 forming part of base 74. The vertical dimension separating the flanges 146 and 148 is equal to or slightly less than the vertical distance separating the top and bottom wall portions 80 and 82 (FIG. 4), respectively, of cover 72. In the illustrated embodiment, a vertically elongated pin 150 passes through the top and bottom wall portions 80 and 82, respectively, of cover 72 as well as through the upper and lower flanges 146 and 148, respectively, of base 74 thereby allowing the cover 72 to pivotally move about a generally vertical axis 152 (FIG. 4) between a closed position, shown in FIGS. 2, 4, 6 and 7, and an open position, shown in FIG. 9.

As will be appreciated, when cover 72 is in a closed position, housing 70 is substantially sealed and inhibited from having liquids escaping therefrom. To enhance the sealing capability of the housing 72 relative to base 74, housing 70 may further include suitable seals arranged about a periphery. The showing of such seals in the drawings, however, has been eliminated for reasons of simplicity.

As shown in FIG. 9, once cover 72 is swung or otherwise moved to an open position, access to the interior cleaning chamber 90 is ready achievable. Moreover, opening the cover 72 permits ready access to and, if desired, removal of a sump 135 from housing 70.

Figure 11:
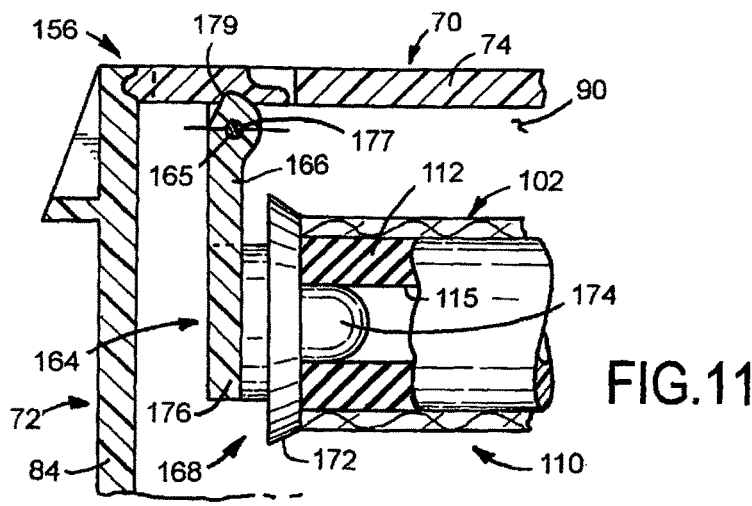
FIG. 11 is an enlarged cross-sectional view taken along line 11-11 of FIG. 4.

Preferably, and shown in FIG. 11, a suitable latch mechanism 156 releasably holds cover 72 in a releasably locked relationship with base 74. Moreover, in a preferred embodiment shown in FIGS. 4, 6, 7 and 10, base 74 is provided with a guide 157 to properly position the cover 72 relative to the base 74 when cover 72 is being closed. Guide 157 preferably has a camming surface 159 to facilitate proper positioning of the cover 72 relative to base 74.

Opening cover 72 furthermore permits access to along with repair and/or replacement of the cleaning member 102 and/or parts of the drive assembly 110. As shown in FIGS. 4 and 7, base 74 of housing 70 includes vertically spaced roller supports 160 and 161. Each roller support 160, 161 has a radially enlarged flange 162 toward one end thereof for limiting transverse movements of the belt 102 on the roller shafts 112, 114 as the drive assembly 110 is operated. The supports 160, 161 preferably provide rotational support for one end of each shaft 112, 114 of the drive assembly 110.

Opposite ends of the shafts 112, 114 are rotatably supported by a displacable support bracket assembly 164. In the embodiment illustrated by way of example in FIGS. 4, 6, 11 and 12, the support bracket assembly 164 includes a vertically rigid member 166 having two vertically spaced but substantially identical head portions 168 and 170 arranged toward opposite vertical ends thereof. As will be appreciated, in this embodiment of the sanitizing and cleaning unit 50, the vertical spacing between the head portions 168 and 170 on bracket assembly 164 is equal to the vertical spacing between the roller supports 160 and 161 (FIG. 4) on base 74. Each head portion 168, 170 extends away from the rigid member 166. Toward a free end thereof, each head portion 168, 170 includes a radially enlarged flange 172 similar to the flanges 162 arranged on the roller supports 160, 161, (FIG. 7). In the embodiment illustrated by way of example, the longitudinal distance separating the flanges 172 on bracket assembly 164 from the flanges 162 on the roller supports 160, 161 is generally equal to the width of the belt 102 entrained about shafts 112, 114. Like the flanges 162 on the roller supports 160, 161 the flanges 172 on the support bracket assembly 164 serve to limit transverse movements of the belt 102 during operation of the sanitizing and cleaning unit 50.

Figure 12:
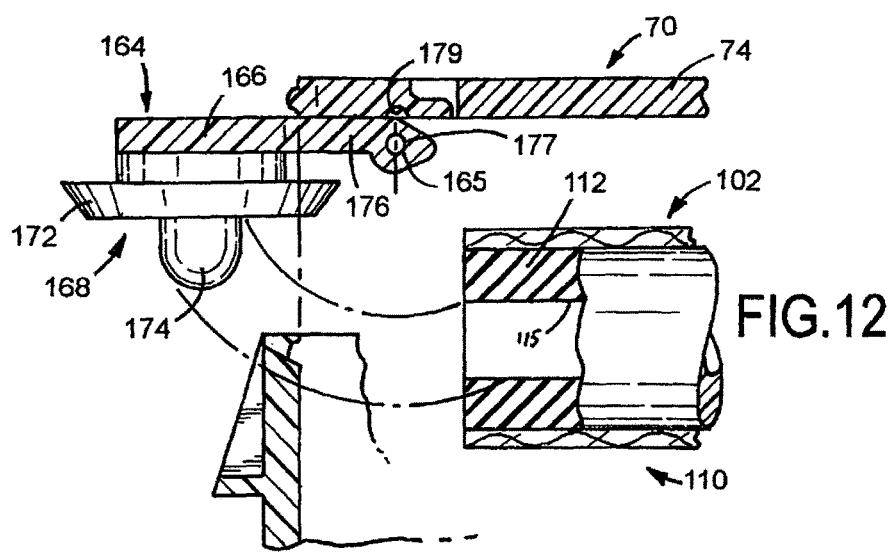
FIG. 12 is a cross-sectional view similar to FIG. 11 but showing components of the sanitizing and cleaning station in disassembled relation relative to each other.

Since the head portions 168 and 170 (FIGS. 4 and 6) on bracket assembly 164 are preferably identical, only head portion 168 will be further described in detail. Turning to FIGS. 11 and 12, each head portion of bracket assembly 164 furthermore preferably includes a free ended pilot 174 extending therefrom, The pilot 174 is sized to snuggly fit within the internal bore or core 115 of each roller shaft 112, 114 supported thereby. Optionally, the free end of each pilot 174 has a semi-spherical configuration to facilitate insertion of the pilot 174 into the open-ended respective core 115 of a roller shaft 112, 114 of rotating assembly 110.

In a preferred form, the support bracket assembly 164 is mounted to readily allow for repair and/or replacement of component pieces thereof. In the form illustrated by way of example in FIG. 10, the support bracket assembly 164 is configured to allow for pivotal movement thereof about a generally vertical axis 165 (FIGS. 11 and 12). In one form, the rigid member 166 of bracket assembly 164 is configured with a rigid mounting arm 176 extending rearwardly from member 166 and is pivotally joined, as by a pin 177 (FIGS. 11 and 12) defining the pivot axis 165 for the bracket assembly 164, to base 74. In one form, a suitable detent mechanism 179 between arm 176 and base 74 of housing 70 releasably maintains the bracket assembly 164 in operative position while permitting the bracket assembly 164 to be pivotally moved relative to base 74 to facilitate repair/replacement of the cleaning member 102.

Figure 13:
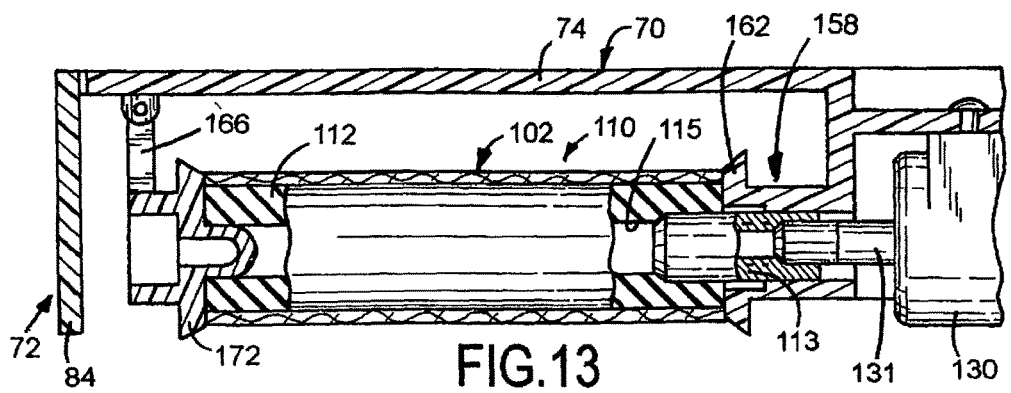
FIG. 13 is a sectional view taken along line 13-13 of FIG. 4.

In the embodiment shown in FIG. 13, drive assembly 110 is preferably driven directly from motor 130. As shown, motor 130 includes a rotatable and free ended output drive shaft 131. In one form, shaft 112 includes a generally hollow stub shaft 113 axially projecting from one end thereof. A lengthwise portion of the stub shaft 113 extends axially within the bore 115 of shaft 112 while another lengthwise portion of shaft 113 extends axially outward from the shaft 112 and into driving relationship with the distal end of the motor drive shaft 131. In one form, stub shaft 113 is journalled for rotation within the roller support 160 on base 74 of housing 70.

To promote and maintain a positive driving relationship between the roller shaft 112 and the output drive shaft 131 of motor 130, the stub shaft 113 preferably has splines axially extending from the free end thereof and along at least that portion of the shaft 113 extending within the hollow core 115 of shaft 112. In the example shown, the remaining outer diameter of the stub shaft 113, journalled for rotation within the roller support 160 on base 74 of housing 70, has a smooth outer diameter. Preferably, the distal end of the output drive shaft 131 of motor 130 also has a splined configuration extending from the free end thereof and extending within the stub shaft 113 to promote a positive driven relationship therebetween.

To inhibit contaminants from inadvertently passing into the interior cleaning chamber 90 of housing 70 through port 92, housing 70 preferably includes a manually operated and displacable door 180 for removably closing the inlet opening 92 to chamber 90 (FIG. 5). In the embodiment illustrated by way of example in FIGS. 2 and 5, the door 180 is arranged for generally vertical displacement along a predetermined path of travel and relative to opening 92 (FIG. 5) in housing 70. In one form, the door 180 is entrapped for sliding movement between a pair of vertical tracks 182 and 184 which also serve to seal the door 180 to the housing 70 when the door 180 is in the closed position. In a preferred embodiment, door 180 is prong loaded toward a closed position. It will be appreciated that a myriad of other designs for closing the opening 92 could be easily and readily embodied without detracting or departing from the broad spirit and novel concept of this invention disclosure.

In this embodiment of the cleaning and sanitizing unit 50, and when a cleaned and sanitized head portion 36 of the stethoscope 32 is removed from the chamber 90 of unit 50, some residual cleaning solution can remain on the head portion 36 of the stethoscope. Accordingly, and in a preferred form of cleaning unit 50, an absorbent pad 190 may be releasably and suitably attached to an exterior of housing 70. Suffice to say, the pad 190 will be formed of a suitable material that will not scratch or otherwise damage the head portion 36 of the stethoscope 32. By such construction, the healthcare provider/care giver can merely swipe the cleaned and sanitized head portion 36 of the stethoscope 32 into contact with the pad 190 to remove any residual cleaning and sanitizing solution which may inadvertently remain thereon. Of course, the releasable association of the pad 190 on housing 70 facilitates disposal of the pad 190 on the housing 70 after each use to avoid inadvertent cross-contamination of the head/chest portion 36 of the stethoscope 32.

Another feature of this invention disclosure relates to the ability to control or eliminate "back contamination" of the stethoscope after the stethoscope has been used on a patient/person whereby furthermore limiting inadvertent transference of an infections between patients/persons. According to this aspect, the present invention disclosure contemplates an apparatus 192 (FIG. 3) for automatically cleaning or otherwise sanitizing the outer surfaces of the cleaning and sanitizing unit or station 50 after the healthcare provider has used the stethoscope on a person/patient. In one form, apparatus 192 can include a movable device which sprays or otherwise radiates a suitable type of disinfectant toward and against the outer surfaces of the housing 70 of the cleaning station or unit 50 to effect cleaning and sanitization of the outer surfaces of the housing 70. In one form, an actuation switch 194 (FIG. 3) on the housing 70 of each cleaning and sanitizing unit 50 can be used to operate apparatus 192 at a suitable time.

Figure 14:
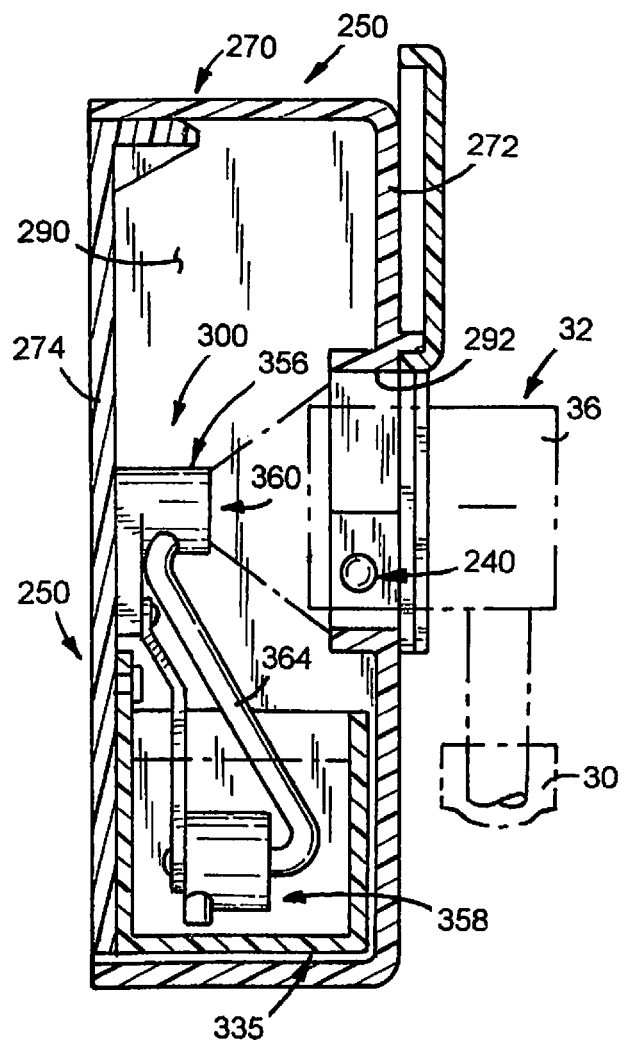
FIG. 14 is an alternative embodiment for the cleaning and sanitizing station.

As mentioned above, the cleaning mechanism for the sanitizing and cleaning unit of this invention disclosure can come in different designs without detracting or departing from the broad spirit and novel scope of this invention disclosure. In this regard, another embodiment of a cleaning and sanitizing station is shown in FIG. 14 and is designated generally by reference numeral 250. The elements or components of this alternative form of cleaning and sanitizing station that are identical or functionally analogous to those components mentioned above with respect to station 50 are designated by the reference numerals similar to those above with the exception this embodiment uses reference numerals in the 200 and 300 series.

In the embodiment shown in FIG. 14, the cleaning and sanitizing station 250 includes a housing 270 including a cover 272 and base 274. Suffice it to say, a head portion 36 of a stethoscope 32 is insertable into an interior cleaning and sanitizing chamber 290 through an inlet opening 292 provided on housing 270.

In the embodiment illustrated in FIG. 14, a cleaning and sanitization mechanism 300 is arranged in the chamber 290 of the cleaning and sanitizing station 250. In this embodiment, the cleaning and sanitization mechanism 300 includes a spray mechanism 356. The spray mechanism 356 includes a motor driven pump assembly 358 having an intake arranged in a sump 335 in the interior of housing 270 and a nozzle-like spray apparatus 360 mounted in the interior chamber 290. As with sump 135 described above, sump 335 is removably arranged within housing 270 for holding a supply of suitable cleaning solution therein. The ability to quickly and readily remove the sump 335 from housing 270 facilitates frequent changing and/or replacement of the cleaning solution within the sump 335. As such, the cleaning solution in the sump 135 can preferably and particularly be suited to the particular infection which may be associated with a particular person/patient being treated and/or examined.

The purpose of the spray apparatus 360 is to direct a predetermined spray pattern toward the head portion 36 of the stethoscope 32 inserted through the port 292 into the cleaning chamber 290 preferably with sufficient pressure to effectively and efficiently clean and sanitize the head portion 36 of the stethoscope 32. It will be appreciated, that the spray pattern directed toward the head portion 36 of the stethoscope 32 is controlled such that the spray cleans and sanitizes the head or chest portion 36 of the stethoscope 32 while no damage is caused thereto. A suitable conduit or passage 364 operably connects the spray mechanism 356 to the pump assembly 358.

As described above, the cleaning and sanitization station 250 furthermore includes a detection mechanism or apparatus 240. The detection mechanism or apparatus 240 is substantially similar regarding either embodiment of the detection mechanism or apparatus 40 described above. Moreover, the detection mechanism or apparatus 240 operates in combination with the identification apparatus 30 operably associated with each stethoscope 32 and operably serves to accomplish the same purposes and ends discussed above regarding detection mechanism or apparatus 40.

Like station 50 discussed above, the sanitizing and cleaning station 250 is preferably selectively operated. That is, the detection mechanism or identity sensor 240 furthermore serves to control operation of the respective sanitizing and cleaning station 250 as a function of when the detection mechanism 240 detects or is otherwise operated to indicate the presence of a head or chest portion 36 of a stethoscope being presented to unit 50 for a cleaning event. In one form, when the detection mechanism or apparatus 240, in whatever form, detects or otherwise functions to indicate the presence of the head or chest portion 36 of the stethoscope is being presented to station 250 for a cleaning and sanitizing event, the detection mechanism 240 operably signals the cleaning mechanism 300 to operate for a predetermined time sufficient to effect a cleaning and sanitization event on the head portion 36 of the stethoscope 32 presented to the cleaning and sanitization station 250.

Figure 15:
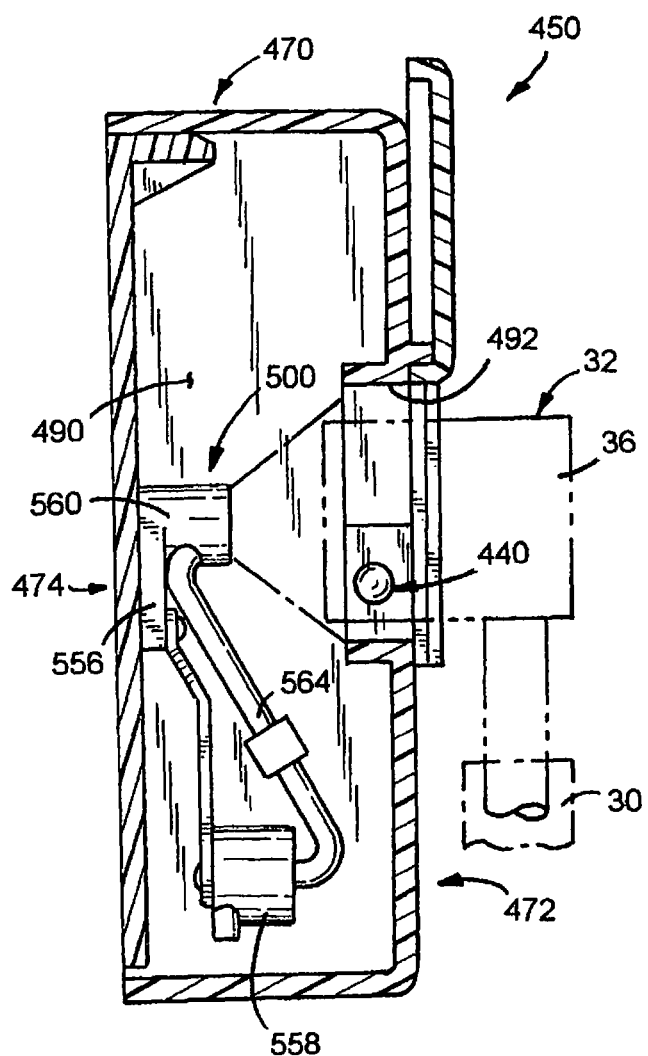
FIG. 15 is another alternative embodiment for the cleaning and sanitizing station.

As mentioned above, the cleaning mechanism for the sanitizing and cleaning unit of this invention disclosure can come in different designs without detracting or departing from the broad spirit and novel scope of this invention disclosure. In this regard, another embodiment of a cleaning and sanitizing station is shown in FIG. 15 and is designated generally by reference numeral 450. The elements or components of this alternative form of cleaning and sanitizing station that are identical or functionally analogous to those components mentioned above with respect to station 50 are designated by the reference numerals similar to those above with the exception this embodiment uses reference numerals in the 400 and 500 series.

In the embodiment shown in FIG. 15, the cleaning and sanitizing station 450 includes a housing 470 including a cover 472 and base 474. In this embodiment, the housing 470 is similar to housing 70 except, in this embodiment, the cover 472 and base 474 do not necessarily have to be sealed relative to each other. Suffice it to say, a head portion 36 of a stethoscope 32 is insertable into an interior cleaning and sanitizing chamber 490 through an inlet opening 492 provided on housing 470.

In the embodiment illustrated in FIG. 15, a cleaning and sanitization mechanism 500 is arranged in the chamber 490 of the cleaning and sanitizing station 450. In this embodiment, the cleaning and sanitization mechanism 500 includes a spray mechanism 556. The spray mechanism 556 includes a motor driven pump assembly 558 arranged in the interior of housing 470 and a nozzle-like spray apparatus 560 mounted in the interior chamber 490. Suitable plumbing 564, preferably arranged within the interior of housing 470, serves to operably interconnect the pump assembly 558 and the spray mechanism 556.

The purpose of the spray apparatus 560 is to direct a spray of air or other suitable disinfectant in whatever form in a predetermined pattern toward the head or chest portion 36 of the stethoscope 32 inserted through the port 492 into the cleaning chamber 490 with sufficient pressure to effectively and efficiently effect cleaning and sanitization of the head portion 36 of the stethoscope 32. It will be appreciated, that the spray pattern directed toward the head or chest portion 36 of the stethoscope 32 is controlled such that the spray cleans and sanitizes the head or chest portion 36 of the stethoscope 32 while no damage is caused thereto. A suitable conduit or passage 564 operably connects the spray mechanism 556 to the pump assembly 558.

As described above, the cleaning and sanitization station 450 furthermore includes a detection mechanism or apparatus 440. The detection mechanism or apparatus 440 is substantially similar to either embodiment of the detection mechanism or apparatus 40 described above. Moreover, the detection mechanism or apparatus 240 operates in combination with the identification apparatus 30 operably associated with each stethoscope 32 and serves to operably accomplish the same purposes and ends discussed above regarding detection mechanism or apparatus 40.

Like station 50 discussed above, the sanitizing and cleaning station 450 is preferably selectively operated. That is, the detection mechanism or identity sensor 440 furthermore serves to control operation of the respective sanitizing and cleaning station 450 as a function of when the detection mechanism or identity sensor 440 detects or is otherwise operated to indicate the presence of a head portion 36 of a stethoscope being presented to unit 50 for a cleaning event. In one form, when the detection mechanism or apparatus 440, in whatever form, detects or otherwise functions to indicate the presence of the head portion 36 of the stethoscope is being presented to station 450 for a cleaning and sanitizing event, the detection mechanism or identity sensor 440 operably signals the cleaning mechanism 500 to operate for a predetermined time period sufficient to effect a cleaning and sanitization event on the head portion 36 of the stethoscope 32 presented to the cleaning and sanitization station 250.

Of course, it will be appreciated other forms of cleaning and sanitizing units could be used as part of the system 10 without detracting or departing from the spirit and broad scope of this invention disclosure. For example, the cleaning and sanitizing unit can be equipped with ultra-violet technology rather than that described in detail above for effecting a cleaning, sanitizing and disinfecting event to the stethoscope.

Optionally, this invention disclosure recognizes, appreciates and takes into consideration a care giver, i.e., a physician, nurse practitioner, nurse, researcher and etc. may not possibly be present everyday in an environment where they necessarily need to use a stethoscope. Unless this possibility, however, is taken into account and consideration, such a lapse in use of a stethoscope having a personal monitor thereon could be mistakenly interpreted as a lack of attention to cleaning and sanitization of that particular stethoscope over that period of non-use. Accordingly, a preferred embodiment of this invention disclosure has been designed and developed to take into consideration and account a wearing event for each stethoscope.

In this regard, and returning to FIG. 1, the system 10 of this invention disclosure furthermore optionally includes an apparatus generally identified by reference numeral 60 for tracking or taking into account usage or a wearing event of each particular stethoscope 32. In a preferred embodiment, apparatus 60 includes a coral 62 for the stethoscopes 32. In one form, such coral 62 is attached to a suitable support S (FIG. 16) preferably situated at a location convenient to a plurality of the care givers/health care providers. In one form, and as shown in FIGS. 1 and 16, the coral 62 includes individualized depositories 62a, 62b, 62c, and etc. which are assigned to a particular health care provider/care giver and, accordingly, to the personalized or individualized stethoscope 32 associated with that particular care giver.

Figure 16:
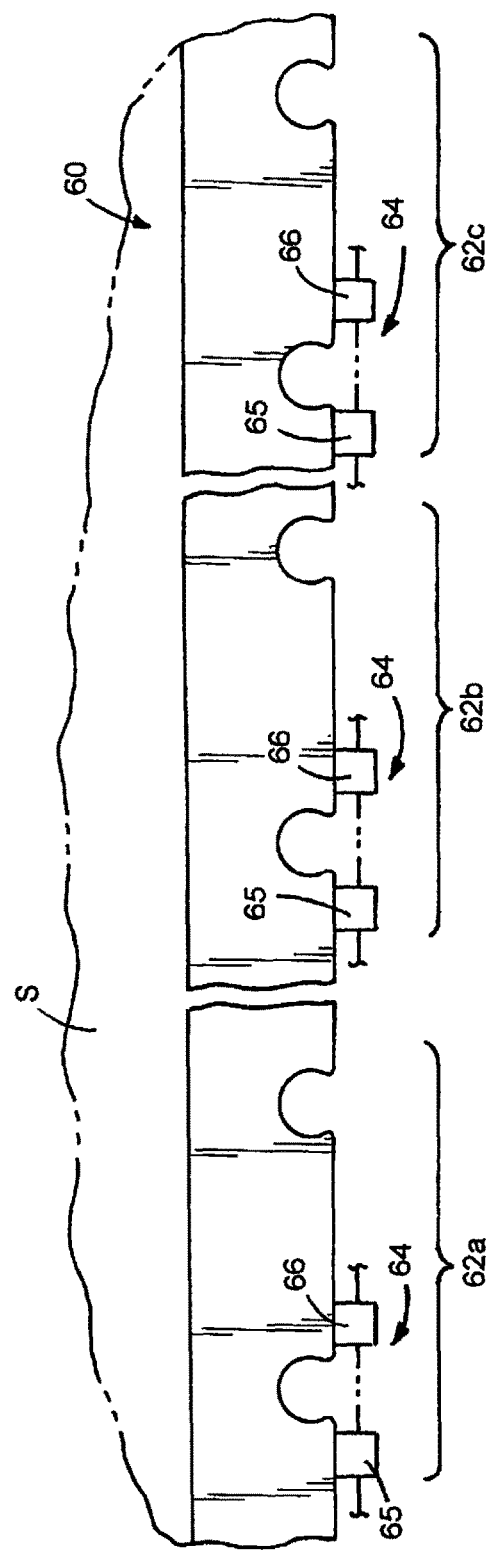
FIG. 16 is an enlarged schematic view of a coral shown in FIG. 1 for releasably holding one or more stethoscopes.

In the embodiment shown by way of example in FIG. 16, each depository 62a, 62b, 62c, and etc. is configured to releasably receive and hold a suitable portion of a particular stethoscope therewithin when such stethoscope is not in use. Preferably, the coral 62 further includes suitable sensor technology 64 associated with each depository 62a, 62b 62c and etc. In one form, such sensor technology 64 may be in the form of a conventional photoelectric sensor including one sensor element 65 for generating a light beam and another sensor element 66 for receiving the light beam. Sensor element 65 may be electrically powered through any suitable source of power. Of course, and as is conventional, when the light beam is broken or otherwise interrupted, indicative of the stethoscope 32 associated with that particular depository being removed therefrom, sensor element 66 delivers a signal to the analysis unit 20 of system 10. As such, a wearing event of each stethoscope 32 in the group of stethoscopes 34 (FIG. 1) can be tracked and recorded. It will be appreciated, any suitable sensor arrangement other the photoelectric sensors illustrated by way of example can be used for detecting when a particular stethoscope is removed and/or returned to the coral 62.

The analysis unit 20 and the plurality of sensors 64 operably associated with apparatus 60 and coral 62 preferably communicate through the conventional wired network described above, for example a local area network (LAN) and wide area network (WAN), or a wireless network, for example a wireless LAN (WLAN) and/or a wireless personal area network (WPAN).

Alternatively, when the identification apparatus 30 is in the form of an RFID device, a suitable sensor or reader can be preferably provided in proximity to an entrance to an examination room or each patient's/person's room in a medical care facility (or other suitable location) so as to automatically detect when the particular stethoscope 32 having the identification apparatus 30 arranged in operable combination therewith moves therepast whereby detecting a wearing event for that particular stethoscope. The wearing events (or lack thereof) measured for that particular stethoscope can then be evaluated by the analysis unit 20 against other work schedules and cleaning events to determine the cleaning and sanitizing efforts of that particular healthcare provider.

Figure 17:
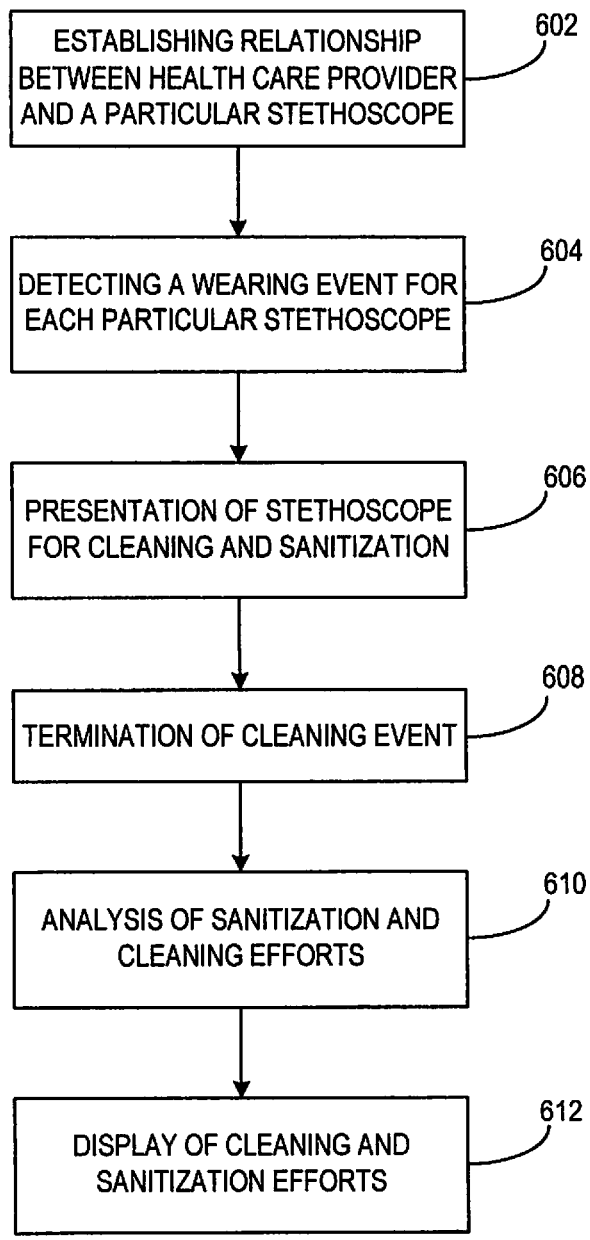
FIG. 17 is a flow chart of a method for monitoring cleaning and sanitization efforts of care givers using stethoscopes according to some embodiments of this invention disclosure.

Turning now to FIG. 17, there is shown a flow chart of one method for monitoring cleaning and sanitization efforts of persons using stethoscopes according to some embodiments of the present invention disclosure. Though the method described involves a process of monitoring cleaning and sanitization efforts of a care giver using a particular stethoscope, it should be appreciated that the process involved can be implemented simultaneously by a plurality of individuals/care givers. Moreover, and while the method described involves a process of monitoring cleaning and sanitization efforts for a conventional stethoscope through use of an apparatus involving those features and elements described above, it should be appreciated the process involved can use devices and technology different from that described above without seriously departing from the novel spirit and broad scope of this invention disclosure.

First, at Step 602, a relationship is established between a health care provider/care giver and a personal stethoscope in a group of stethoscopes. In the example shown in FIG. 1, the identification apparatus or device 30 operably associated with a personal or particular stethoscope 32 serves to identify in that stethoscope 32 in the group 34 of conventional stethoscopes As such, and by being operably associated with a particular stethoscope, the identification apparatus or device 30 furthermore serves to identify the particular healthcare provider associated with that particular stethoscope. Optionally, the identification apparatus or device 30 on the particular stethoscope matches an ID associated with a user profile managed by the analysis unit 20 of system 10. As mentioned above, such identification apparatus or device 30 can be in the form of a tag or the like having a readable code imprinted or otherwise provided thereon or an RFID device which automatically identifies to a reader a particular stethoscope 32 in the group of stethoscopes 34.

At step 604, a wearing event of a particular stethoscope in the group of stethoscopes 36 is monitored. That is, at Step 604 the removal of any stethoscope 32 from the coral or apparatus 60 is detected and/or read and a signal is delivered or otherwise transferred to the analysis unit 20 indicative of a wearing event for that particular stethoscope. Optionally, and when a particular stethoscope having an RFID device operably associated therewith passes a reader or the like, such action or wearing event associated with that particular stethoscope 32 is monitored and the signal delivered to the analysis unit 20 allows unit 20 to operably calculate the date and time when the particular stethoscope was being worn or otherwise used by the healthcare provider. Also at Step 604, the termination of such wearing event can be read or otherwise sensed and a signal delivered to unit 20 to allow unit 20 to operably calculate the date and time associated with the termination of such a wearing event.

As such, the analysis unit 20 optionally takes into account the time during which cleaning events for that particular stethoscope were to be recorded and the frequency of such cleaning events calculated. Preferably, unit 20 is configured to calculate the cleaning events to which a particular stethoscope was subjected during the working hours of the healthcare provider associated with the particular stethoscope and not during other time periods of non-use, i.e., vacation days, sick days and other time periods wherein the healthcare provider would not necessarily be required to use their particular stethoscope.

At Step 606, and during use thereof, the stethoscope 32 is presented to the cleaning and sanitization station 50 to effect a cleaning event. That is, when a particular stethoscope is presented to the cleaning and sanitization station 50 to effect a cleaning event, the identification apparatus 30, in whatever form, operably associated with the particular stethoscope is read or otherwise sensed by the detection mechanism or apparatus 40, in whatever form, and a signal is transferred or otherwise delivered to the analysis unit 20. Optionally, and when a particular stethoscope is presented to the cleaning and sanitizing station 50 to effect a cleaning event, the code on the particular stethoscope is read or otherwise sensed by the detection mechanism or apparatus 40, in whatever form, and the signal delivered to the analysis unit 20 allows the analysis unit 20 to operably calculate the date and time when the particular stethoscope was presented to the cleaning unit 50 to effect a cleaning event thereon.

Figure 18:
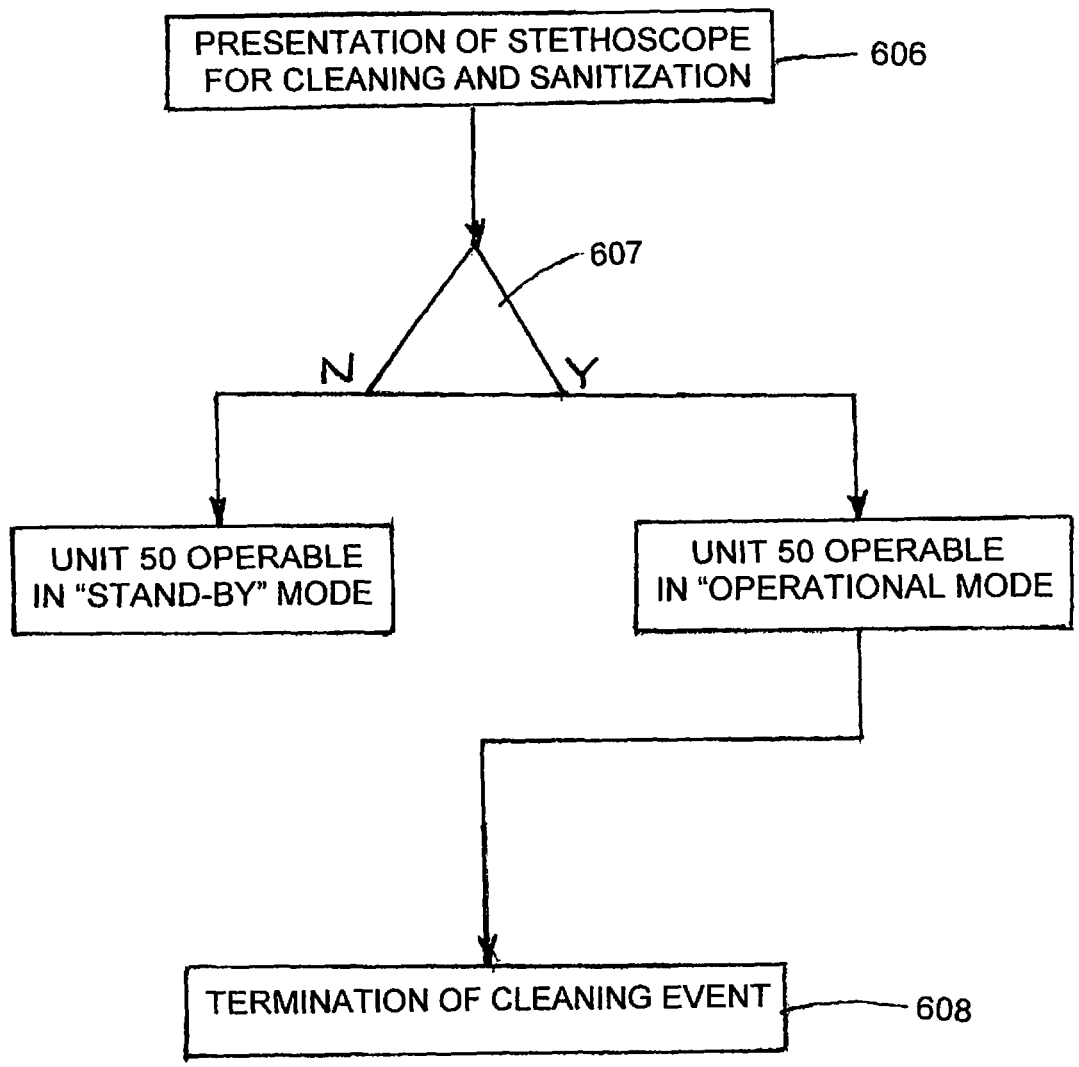
FIG. 18 schematically an alternative Step in the method for monitoring cleaning and sanitization efforts of care givers using stethoscopes according to some embodiments of this invention disclosure.

As mentioned above, when the identification apparatus 30, in whatever form, operably associated with the particular stethoscope is read or otherwise sensed by the detection mechanism or apparatus 40, in whatever form, operation of the cleaning and sanitization unit 50 preferably changes operation. As illustrated in FIG. 18, at Step 607, and when the detection mechanism or apparatus 40 senses the identification apparatus 30 on the stethoscope is within a predetermined range, operation of the cleaning and sanitization unit 50 switches to an "operational" mode whereby allowing a cleaning and sanitization event to be effected on the head portion of the stethoscope presented to unit 50. On the other hand, at Step 607, when the detection mechanism or apparatus 40 senses the identification apparatus 30 on the stethoscope is outside a predetermined range of operation of the cleaning and sanitization unit 50 is switched to a "stand-by" mode.

At Step 608, and following a cleaning event being performed thereon, the particular stethoscope 32 is withdrawn or retracted from the cleaning and sanitizing unit 50. At Step 608, the retraction or removal of the stethoscope relative to the cleaning and sanitizing unit 50 is detected by the code on the particular stethoscope being read or otherwise sensed by the detection mechanism or apparatus 40, in whatever form, and a signal is transferred to the analysis unit 20. Optionally, and when a particular stethoscope is retracted or otherwise withdrawn relative to the cleaning and sanitizing station 50 to terminate the cleaning event, the detection mechanism or apparatus 40, in whatever form, delivers or otherwise transfers a signal to the analysis unit 20 indicative of the termination of the cleaning and sanitizing event.

At Step 610, the analysis unit 20 operably calculates the cleaning and sanitization efforts of each health care provider/care giver relative to each particular stethoscope 32 in the group of stethoscopes 36. That is, the analysis unit 20 calculates the cleaning and sanitization efforts of each health care provider/care giver relative to each particular stethoscope 32 in the group of stethoscopes 36 using the information inputted thereto from the plurality of sensors and indicators forming part of system 20. Optionally, and to accurately test the compliance of the care giver's cleaning and sanitization efforts with given standards while also testing the quality of the cleaning and sanitization events, the analysis unit 20 takes into account the duration of the cleaning and sanitizing event was recorded as well as the frequency of the cleaning and sanitization events. As mentioned, cleaning events which are missing from certain episodes are calculated by unit 20 and can be compared against the work schedule of the particular care giver. Optionally, unit 20 is configured to calculate performance levels of each care giver so as to reflect the care giver's attention to stethoscope cleanliness and sanitization habits. Optionally, such performance levels can be compared by unit 20 against a given standard whereby allowing yielding a compliance comparison with such standard. For example, a predetermined pattern of how many visits may occur for a given doctor's office may be compared to the number of cleaning events actually occurring at such an office whereby determining the care giver's attention to stethoscope cleanliness and sanitization habits at such office. The scoring bases for and the results calculated by the analysis unit 20 can be optionally stored in the repository 25 of unit 20

At Step 612, the computed and comparative results developed by the analysis unit 20 can be selectively printed and displayed. Alternatively, and at Step 612, a report may be sent or otherwise generated and/or delivered to a particular care giver and/or others indicating the sanitization and cleaning efforts being made regarding each of the stethoscopes in the group of stethoscopes.

From the foregoing, it will be observed that numerous modifications and variations can be made and effected without departing or detracting from the true spirit and novel concept of this invention disclosure. Moreover, it will be appreciated, the present disclosure is intended to set forth exemplifications which are not intended to limit the disclosure to the specific embodiments illustrated. Rather, this disclosure is intended to cover by the appended claims all such modifications and variations as fall within the spirit and scope of the claims.

What is claimed is:

1. A system for monitoring cleaning efforts of care givers using stethoscopes, said system comprising:
   one or more cleaning stations, with each station including a housing and cleaning apparatus disposed within said housing, with said cleaning apparatus being structured to clean a head portion of a stethoscope presented thereto;
   an identification apparatus operably associated with each of a plurality of stethoscopes for identifying each particular stethoscope;
   an apparatus for detecting each time the identification apparatus operably associated with a particular stethoscope is presented to the cleaning apparatus to effect a cleaning event;
   a networked system operably connected with each cleaning station, with said networked system including an analysis unit operably connected to said detecting apparatus and configured for calculating the cleanliness level of each particular stethoscope having the identification apparatus operably associated therewith;
   with said networked system further including a monitoring apparatus operably connected to said analysis unit for taking into account actual usage of any one of said stethoscopes having said identification apparatus operably associated therewith and configured to develop data indicative of a wearing event for said stethoscope, with the cleanliness level of said stethoscope being at least partially determined by the data generated by said monitoring apparatus; and
   a network repository for storing each time a particular stethoscope is presented to a cleaning apparatus for a cleaning event.

2. The system for monitoring cleaning efforts of care givers using stethoscopes according to claim 1, wherein each cleaning event is recorded only after the detecting apparatus detects the presence of the cleaning head of a particular stethoscope in one of said cleaning stations for a predetermined time period.

3. The system for monitoring cleaning efforts of care givers using stethoscopes according to claim 1, further including an apparatus operably connected to said analysis unit for providing an indication of the cleanliness level of any particular stethoscope in the group of stethoscopes based on the number of cleaning events to which said particular stethoscope was subjected.

4. The system for monitoring cleaning efforts of care givers using stethoscopes according to claim 1, wherein the housing of each cleaning station includes an enclosure defining a port through which the head portion of the stethoscope moves to effect the cleaning event; and wherein said detection apparatus is arranged and positioned to sense the ingress and egress of the head portion of the stethoscope through said port.

5. The system for monitoring cleaning efforts of care givers using stethoscopes according to claim 1, wherein the analysis unit is configured to calculate cleanliness levels of both cleaned and uncleaned stethoscopes having the identification apparatus operably associated therewith.

6. A system for monitoring cleaning efforts of care givers using stethoscopes, said system comprising:
- a plurality of networked cleaning stations disposed at different locations throughout a facility, with each cleaning station including a housing and a cleaning apparatus disposed within said housing, with said cleaning apparatus being structured to clean a head portion of a stethoscope presented thereto;
- an identification apparatus operative to identify an individual stethoscope in a group of stethoscopes;
- an apparatus associated with each cleaning station, with said apparatus being designed and configured to: detect the identity of each stethoscope being presented to any of said cleaning stations for cleaning during a cleaning event; monitor and detect each time an individual stethoscope is presented to one of said cleaning stations for a cleaning event; and calculate a duration of each cleaning event that has happened to an identified stethoscope at any of said cleaning stations; and
- an analysis unit configured to use data from said apparatus associated with each cleaning station to determine the cleanliness level of each stethoscope having the identification apparatus attached thereto partly as a function of the number of cleaning events detected by said apparatus at one or more of said cleaning stations compared against a fixed value.

7. The system for monitoring cleaning efforts of care givers using stethoscopes according to claim 6, wherein each cleaning event is recorded after the said apparatus senses the presence of the cleaning head of a particular stethoscope relative to one of the cleaning stations for a predetermined time period.

8. The system for monitoring cleaning efforts of care givers using stethoscopes according to claim 6, further including a repository for storing each time a particular stethoscope is presented to one of said cleaning stations for a cleaning event.

9. The system for monitoring cleaning efforts of care givers using stethoscopes according to claim 6, further including an apparatus operably connected to said analysis unit and operative to monitor a wearing event for each stethoscope, and wherein the cleaning efforts for a particular stethoscope are partially evaluated as a function of the number of wearing events detected by said apparatus for monitoring wearing events.

10. The system for monitoring cleaning efforts of care givers using stethoscopes according to claim 6, further including an apparatus operably connected to said analysis unit for displaying an indication of the cleanliness level of a particular stethoscope.

11. The system for monitoring cleaning efforts of care givers using stethoscopes according to claim 6, wherein the housing of each cleaning apparatus at each of said cleaning stations defines a port through which the head portion of the stethoscope moves to effect the cleaning event; and wherein said identification apparatus is arranged in a position to sense the ingress and egress of the head portion of the stethoscope through said port.

12. The system for monitoring cleaning efforts of care givers using stethoscopes according to claim 6, wherein said identification apparatus operably associated with each stethoscope in said group of stethoscopes includes an RFID device.

13. A system for monitoring cleaning efforts of care givers using stethoscopes, said system comprising:
- one or more cleaning stations, with each station including a cleaning apparatus structured to clean a head portion of a stethoscope presented thereto;
- an identification apparatus operably associated with each of a plurality of stethoscopes for identifying each particular stethoscope;
- a first apparatus configured to detect and generate a signal indicative of when a stethoscope having an identification apparatus comes within a specified radius of a cleaning station;
- a second apparatus configured to monitor and generate a signal each time the identification apparatus operably associated with a particular stethoscope is presented to the cleaning apparatus to effect a cleaning event;
- a third apparatus configured to generate a signal indicative of whether said particular stethoscope having said identification apparatus operably associated therewith is timely presented to an adjacent cleaning station for a cleaning event, and wherein said timely presentation of said particular stethoscope to be cleaned requires said particular stethoscope to be presented to said cleaning station within a predetermined period of time following said first apparatus detecting when a particular stethoscope having an identification apparatus operably associated therewith comes within a specified radius of a cleaning station; and
- an analysis unit operably connected to said each apparatus and configured for calculating the cleanliness level of each particular stethoscope having the identification apparatus operably associated therewith.

* * * * *